US009896622B2

(12) United States Patent
You et al.

(10) Patent No.: US 9,896,622 B2
(45) Date of Patent: Feb. 20, 2018

(54) COUMARIN-BASED DERIVATIVE COMPOUND, PREPARING METHOD THEREOF, AND FLUORESCENT COMPOSITION CONTAINING THE SAME

(71) Applicant: Ewha University—Industry Collaboration Foundation, Seoul (KR)

(72) Inventors: Youngmin You, Seoul (KR); Byunghak Jhun, Cheonan-si (KR)

(73) Assignee: EWHA UNIVERSITY—INDUSTRY COLLABORATION FOUNDATION, Seoul (KR)

( * ) Notice: Subject to any disclaimer, the term of this patent is extended or adjusted under 35 U.S.C. 154(b) by 0 days.

(21) Appl. No.: 15/449,259

(22) Filed: Mar. 3, 2017

(65) Prior Publication Data
US 2017/0253794 A1    Sep. 7, 2017

(30) Foreign Application Priority Data

Mar. 3, 2016  (KR) .................. 10-2016-0025918
Feb. 17, 2017  (KR) .................. 10-2017-0021736

(51) Int. Cl.
*C09K 11/06*  (2006.01)
*C07D 311/16*  (2006.01)
*C09K 11/02*  (2006.01)
*H01L 51/00*  (2006.01)

(52) U.S. Cl.
CPC ............ *C09K 11/06* (2013.01); *C07D 311/16* (2013.01); *C09K 11/025* (2013.01); *H01L 51/0042* (2013.01); *H01L 51/0073* (2013.01); *C09K 2211/1007* (2013.01); *C09K 2211/1011* (2013.01); *C09K 2211/1088* (2013.01)

(58) Field of Classification Search
CPC .................. C09K 11/06; C09K 11/025; C09K 2211/1007; C09K 2211/1011; C09K 2211/10088; C07D 311/16; H01L 51/0042; H01L 51/0073
USPC .................. 514/314, 457; 549/280, 290, 284
See application file for complete search history.

(56) References Cited

U.S. PATENT DOCUMENTS 5,260,457 A * 11/1993 Nishida ................ C07D 311/10
                                                         549/290
8,716,496 B2    5/2014 Drevelle et al.
(Continued)

FOREIGN PATENT DOCUMENTS

JP    2010059417 A    3/2010
JP    5920995        4/2016
(Continued)

OTHER PUBLICATIONS

Haruka Sakai, Tomoya Hirano, Shuichi Mori, Shinya Fujii, Hiroyuki Masuno, Marie Kinoshita, Hiroyuki Kagechika, and Aya Tanatani, 6-Arylcoumarins as Novel Nonsteroidal Type Progesterone Antagonists: An Example with Receptor-Binding-Dependent Fluorescence, J. Med. Chem. 2011, 54, 7055-7065, r2011 American Chemical Society.*
(Continued)

*Primary Examiner* — Bijan Ahvazi
(74) *Attorney, Agent, or Firm* — Cantor Colburn LLP

(57) ABSTRACT

Disclosed herein are a coumarin-based derivative compound, a preparation method thereof, and a fluorescent composition containing the same.

19 Claims, 12 Drawing Sheets
(8 of 12 Drawing Sheet(s) Filed in Color)

(56) References Cited

U.S. PATENT DOCUMENTS

2006/0063806 A1* 3/2006 Lin .................. C07D 311/18
  514/314
2014/0234884 A1 8/2014 Drevelle et al.
2016/0343954 A1 11/2016 Seo et al.

FOREIGN PATENT DOCUMENTS

KR 101129574 3/2012
WO 2015026935 A2 2/2015

OTHER PUBLICATIONS

Hea Jung Park, et al., "Novel Naphthalene Based Lariat-Type Crown Ethers Using Direct Single Electron Transfer Photochemical Strategy", Bull. Korean Chem. Soc., (2013), vol. 34, No. 12, pp. 3681-3689.
Huaning Zhu, et al., "Tetrahydro[5]-helicene-Based Imide Derivatives", Scientific Reports, (Apr. 14, 2016), vol. 6, pp. 1-12.
Serguei V. Feskov, et al., "Magnetic Field Effects in Fluorescence of Exciplex and Fluorophore for the Weller Schemes I and II: Similarities and Differences", The Journal of Physical Chemistry C, (2014), vol. 118, pp. 21365-21376.
Donghee Kim et al., One-Pot Catalysis of Dehydrogenation of Cyclohexano nes to Phenols and Oxidative Heck Coupling: Expedient Synthesis of Coumarins, 2013, p. S1-S50, Issue 38, Chem. Commun.
Korean office Action for Application No. 10-2017-0021736 dated Dec. 15, 2017.

* cited by examiner

COUMARIN-BASED DERIVATIVE COMPOUND, PREPARING METHOD THEREOF, AND FLUORESCENT COMPOSITION CONTAINING THE SAME

CROSS-REFERENCE TO RELATED APPLICATION

This application claims priority to and the benefit of Korean Patent Application No. 10-2016-0025918 and 10-2017-0021736 filed in the Korean Intellectual Property Office on Mar. 3, 2016 and Feb. 17, 2017, the entire contents of which are incorporated herein by reference.

BACKGROUND (a) Field

The present invention relates to a coumarin-based derivative compound, a preparation method thereof, and a fluorescent composition containing the same.

(b) Description of the Related Art

Various fluorescent compounds have been developed based on 1-benzopyran-2-one (coumarin) platform. This platform is non-fluorescent, and provides a photoluminescence quantum yield (PLQY) of 0.001 or less in cyclohexane. Non-emissive properties of coumarin originate from a presence of a carbonyl moiety. Photophysical mechanism by which carbonyl groups quench fluorescence emission remains an intensive research subject.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a coumarin-based derivative compound, a preparation method thereof, and a fluorescent composition containing the same.

However, aspects of the present disclosure are not limited to the above-mentioned aspects. That is, other aspects that are not mentioned may be obviously understood by those skilled in the art from the following specification.

A first exemplary embodiment of the present invention provides a coumarin-based derivative compound represented by the following Chemical Formula 1:

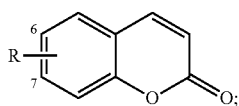

[Chemical Formula 1]

in Chemical Formula 1, R, a substituent positioned at the 6-position or 7-position of a coumarin ring of Chemical Formula 1, includes a $C_{6-50}$ aryl group.

A second exemplary embodiment of the present invention provides a preparation method of a coumarin-based derivative compound, the preparation method including reacting a coumarin-based compound represented by Chemical Formula 2 with $C_{6-50}$ aryl boronic acid in the presence of a palladium catalyst:

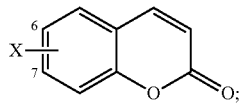

[Chemical Formula 2]

in Chemical Formula 2, X is halogen positioned at the 6-position or 7-position of a coumarin ring of Chemical Formula 2.

A third exemplary embodiment of the present invention provides a fluorescent composition containing the coumarin-based derivative compound according to the first exemplary embodiment of the present invention.

According to the embodiment of the present invention, a novel coumarin-based compound having strong fluorescence emission characteristics may be prepared by reacting the coumarin-based compound with $C_{6-50}$ aryl boronic acid.

The coumarin-based compound according to the exemplary embodiment of the present invention may be doped on a semiconducting polymer, such that a quantum yield thereof may be increased or a color of a fluorescence emission or wavelength thereof may be changed, and thus, the coumarin-based compound may be utilized in a fluorescent dye, or the like.

BRIEF DESCRIPTION OF THE DRAWINGS

The patent or application file contains at least one drawing executed in color. Copies of this patent or patent application publication with color drawing(s) will be provided by the Office upon request and payment of the necessary fee

DETAILED DESCRIPTION OF THE EMBODIMENTS

Figure 1:
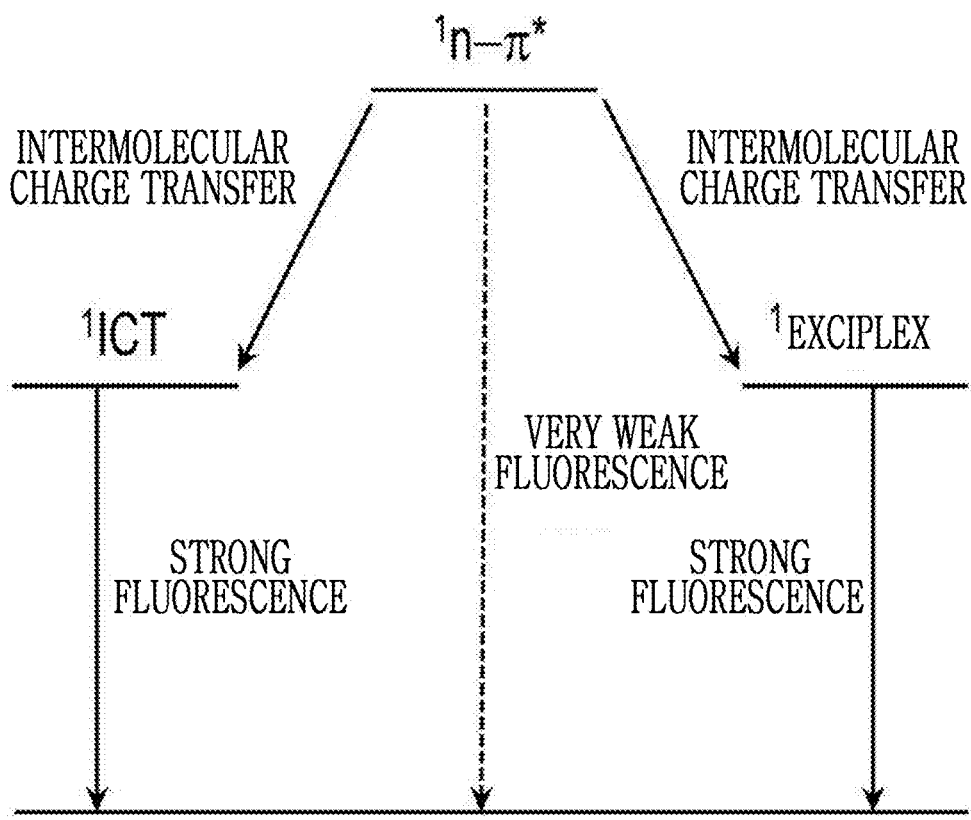
FIG. 1 is a schematic view illustrating two molecular strategies for achieving strong fluorescence emission from a non-fluorescent n-π* fluorophore in an exemplary embodiment of the present invention.

Hereinafter, exemplary embodiments of the present invention will be described in detail with reference to the accompanying drawings so as to be easily practiced by those skilled in the art to which the present invention pertains. However, the present invention may be implemented in several different forms and is not limited to exemplary embodiments provided in the present specification. In addition, components unrelated to a description will be omitted in the accompanying drawings in order to clearly describe the present invention, and similar reference numerals will be used to denote similar components throughout the present specification.

Throughout the present specification and the claims that follow, when it is described that an element is "coupled" to another element, the element may be "directly coupled" to the other element or "electrically coupled" to the other element through a third element.

Throughout the present specification, when it is mentioned that any member is positioned "on" another member, it may mean that any member comes in contact with another member, or still another member are present between two members.

In addition, throughout the present specification, unless explicitly described to the contrary, the word "comprise" and variations such as "comprises" or "comprising", will be understood to imply the inclusion of stated elements but not the exclusion of any other elements. Throughout the present specification, the terms of degree, such as "about", "substantially", and the like, are used in the sense of "perfectly, or nearly perfectly, when given the manufacturing and material tolerances inherent in the stated circumstances" and are used to prevent an unscrupulous infringer from unfairly taking advantage of the invention disclosure where exact or absolute figures are stated as an aid to understanding the invention. Throughout the present specification, the term "~ step" or "step of ~" does not means "step for ~".

Throughout the present specification, the term "combination(s) of" included in Markush type description, which means mixture(s) or combination(s) of one or more components selected from a group consisting of components described in Markush type description, means that the disclosure includes one or more components selected from the group consisting of the components.

Throughout the present specification, the term "A and/or B" means "A or B, or A and B".

Throughout the present specification, the term "aryl" means a monocyclic or bicyclic aromatic ring such as a fused bicyclic aromatic ring, for example, naphthyl, phenanthrenyl, or the like, as well as the monocyclic aromatic ring, for example, phenyl, substituted phenyl, or the like. Therefore, an aryl group contains at least one ring having at least six atoms, five or less rings contain 50 or less atoms, and a double bond alternates (resonates) between adjacent carbon atoms or suitable hetero atoms. The aryl group may be arbitrarily substituted with one or more groups among groups which include halogen, alkyl, alkoxy, hydroxyl, carboxyl, carbamoyl, alkyloxycarbonyl, nitro, trifluoromethyl, amino, cycloalkyl, cyano, alkyl S(O)$_m$ (m=0, 1, 2), or thiol, but are limited thereto. For example, throughout the present specification, a substituted or un-substituted $C_{6-50}$ aryl group may be selected from the group consisting of a benzene ring, a toluene ring, a naphthalene ring, an anthracene ring, a phenanthrene ring, a pentalene, an indene ring, a biphenylene ring, a phenalene ring, an azulene ring, a heptalene, an acenaphthylene ring, a fluorene ring, a tetracene ring, a triphenylene ring, a pyrene ring, a chrysene ring, an ethyl-chrysene ring, a picene ring, a perylene ring, a pentaphene ring, a pentacene ring, a tetraphenylene ring, a hexaphene ring, a hexacene ring, a rubicene ring, a coronene ring, a trinaphthylene ring, a heptaphene ring, a heptacene ring, a pyranthrene ring, an ovalene ring, a fluoranthene ring, a benzofluoranthene ring, a 9-anthryl group, a 2-anthryl group, a 9-phenanthryl group, a 2-phenanthryl group, a 1-pyrenyl group, a chrysenyl group, a naphthacenyl group, a coronyl group, and derivatives thereof, but is not limited thereto. For example, throughout the present specification, the term "aryl" may be a phenyl group, a benzyl group, an anthryl group, a naphthyl group, or a phenanthryl group as a $C_{6-50}$ aryl group, but is not limited thereto.

Hereinafter, exemplary embodiments and Examples according to the present invention will be described in detail with reference to the accompanying drawings. However, the present invention is not limited to the exemplary embodiments, the Examples, and the accompanying drawings.

A first example embodiment of the present invention provides a coumarin-based derivative compound represented by the following Chemical Formula 1:

[Chemical Formula 1]

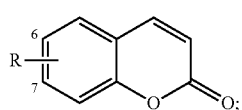

in Chemical Formula 1, R, a substituent positioned at the 6-position or 7-position of a coumarin ring of Chemical Formula 1, includes a $C_{6-50}$ aryl group.

Throughout the present specification, the term "aryl" means the monocyclic or bicyclic aromatic ring such as the fused bicyclic aromatic ring, for example, naphthyl, phenanthrenyl, or the like, as well as the monocyclic aromatic ring, for example, phenyl, substituted phenyl, or the like, and may be the phenyl group, the benzyl group, the anthryl group, the naphthyl group, or the phenanthryl group as the $C_{6-50}$ aryl group, but is not limited thereto.

In the exemplary embodiment of the present invention, in Chemical Formula 1, R, which is the substituent positioned at the 6-position or 7-position of the coumarin ring of Chemical Formula 1, may include a $C_{6-50}$ aryl group, a $C_{6-40}$ aryl group, a $C_{6-30}$ aryl group, or a $C_{6-20}$ aryl group, but is not limited thereto.

In the exemplary embodiment of the present invention, the aryl group may include at least one of the phenyl group, the anthryl group, the naphthyl group, the phenanthryl group, an indene group, an azulene group, a fluorenyl group, a tetracene group, a triphenylene group, a pyrene group, a chrycene group, a pentacene group, a tetraphenylene group, a hexaphene group, a rubicene group, a coronene group, a trinaphthylene group, a pyranthrene group, a fluoranthene group, a benzofluoranthene group, a naphthacene group, and a coronyl group, but is not limited thereto.

In the exemplary embodiment, the coumarin-based derivative compound, includes at least one of

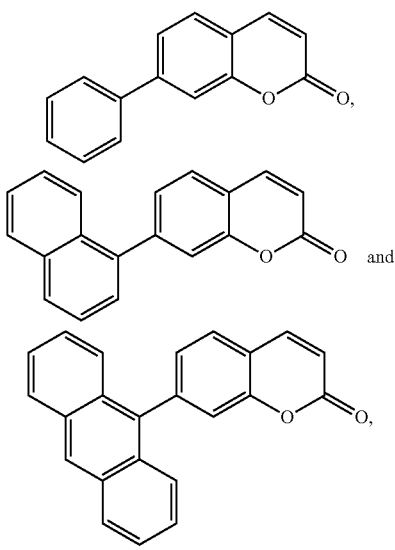

but is not limited thereto.

A second exemplary embodiment of the present invention provides a preparation method of a coumarin-based derivative compound, the preparation method including reacting a coumarin-based compound represented by Chemical Formula 2 with $C_{6-50}$ aryl boronic acid in the presence of a palladium catalyst:

[Chemical Formula 2]

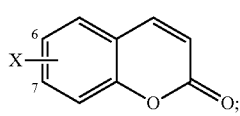

in Chemical Formula 2, X is halogen positioned at the 6-position or 7-position of a coumarin ring of Chemical Formula 2.

In the exemplary embodiment of the present invention, the aryl group may include at least one of the phenyl group, the anthryl group, the naphthyl group, the phenanthryl group, the indene group, the azulene group, the fluorenyl group, the tetracene group, the triphenylene group, the pyrene group, the chrycene group, the pentacene group, the tetraphenylene group, the hexaphene group, the rubicene group, the coronene group, the trinaphthylene group, the pyranthrene group, the fluoranthene group, the benzofluoranthene group, the naphthacene group, and the coronyl group, but is not limited thereto.

In the exemplary embodiment of the present invention, the coumarin-based derivative compound, includes at least one of

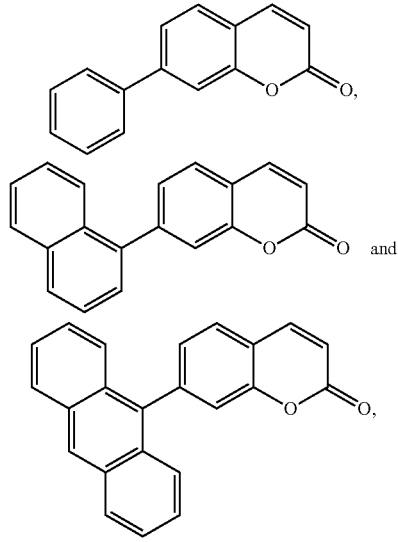

but is not limited thereto.

A third exemplary embodiment of the present invention provides a fluorescent composition containing the coumarin-based derivative compound according to the first exemplary embodiment. A detailed description of contents of the fluorescent composition according to the third exemplary embodiment of the present invention overlapping those of the coumarin-based derivative compound according to the first exemplary embodiment of the present invention is omitted. However, although the description is omitted, the contents described in the first exemplary embodiment of the present invention may be equally applied to the third exemplary embodiment of the present invention.

In the exemplary embodiment of the present invention, the coumarin-based derivative compound may be represented by the following Chemical Formula 1:

[Chemical Formula 1]

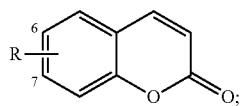

in Chemical Formula 1, R, the substituent positioned at the 6-position or 7-position of a coumarin ring of Chemical Formula 1, includes the $C_{6-50}$ aryl group.

In the exemplary embodiment of the present invention, in Chemical Formula 1, R, which is the substituent positioned at the 6-position or 7-position of the coumarin ring of Chemical Formula 1, may include the $C_{6-50}$ aryl group, the $C_{6-40}$ aryl group, the $C_{6-30}$ aryl group, or the $C_{6-20}$ aryl group, but is not limited thereto.

In the exemplary embodiment of the present invention, the aryl group may include at least one of the phenyl group, the anthryl group, the naphthyl group, the phenanthryl group, the indene group, the azulene group, the fluorenyl group, the tetracene group, the triphenylene group, the pyrene group, the chrycene group, the pentacene group, the tetraphenylene group, the hexaphene group, the rubicene group, the coronene group, the trinaphthylene group, the pyranthrene group, the fluoranthene group, the benzofluoranthene group, the naphthacene group, and the coronyl group, but is not limited thereto.

In the exemplary embodiment of the present invention, the coumarin-based derivative compound,
includes at least one of

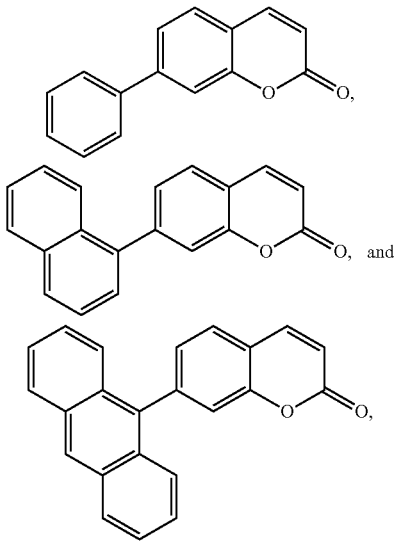

but is not limited thereto.

In the exemplary embodiment of the present invention, the fluorescent composition may additionally contain a semiconducting polymer, but is not limited thereto. For example, the fluorescent composition may be prepared by doping the semiconducting polymer with the coumarin-based derivative compound, but is not limited thereto.

In the exemplary embodiment of the present invention, the semiconducting polymer may include at least one of a poly(N-vinylcarbazole) (PVK)-based polymer, a poly(aniline)-based polymer, a poly(pyrrole)-based polymer, and a poly(thiophene)-based polymer, and include any polymer having hole transporting ability.

In the exemplary embodiment of the present invention, the fluorescent composition may additionally contain an electron donor dopant, but is not limited thereto. For example, the electron donor dopant may be one or more selected from the group consisting of 1,2-dimethylindole (DMI), N,N-dimethylaniline (DMA), and N,N-dimethyl-p-toluidine (DMT), but is not limited thereto.

In the exemplary embodiment of the present invention, as the number of carbon atoms in the aryl ring included in the coumarin-based derivative compound is increased, a quantum yield of the coumarin-based derivative compound may be increased, or a fluorescence emission color or wavelength may be changed, but the present invention is not limited thereto. For example, as the number of carbon atoms in the aryl ring included in the coumarin-based derivative compound is increased, a photoluminescence quantum yield of the coumarin-based derivative compound may be improved, but the present invention is not limited thereto.

In the exemplary embodiment of the present invention, the coumarin-based derivative compound is doped on the semiconducting polymer, such that the fluorescence emission color or wavelength of the coumarin-based derivative compound may be changed, but the present invention is not limited thereto. For example, the coumarin-based derivative compound is doped on the semiconducting polymer, such that the photoluminescence quantum yield of the coumarin-based derivative compound may be improved, but the present invention is not limited thereto.

In the present specification, execution of basic strategies for generating fluorescence of coumarin-based derivative compounds is reported. FIG. 1 is a schematic view illustrating two molecular strategies for achieving strong fluorescence emission from a non-fluorescent n-π* fluorophore in an exemplary embodiment of the present invention.

Strong fluorescence emission may be achieved by providing the coumarin-based derivative compound containing the aryl group. This compound facilitates strong charge separation, and generates an intramolecular charge-transfer (ICT) state.

An ICT singlet state may be located below an n-π* singlet state depending on oxidation potentials of aromatic units. Aromatic units having low band gap energy may effectively be aligned with the coumarin levels to enable this radiative process. Aromatic hydrocarbons with extended π conjugation may donate electrons to electron-deficient coumarin upon photoexcitation, promoting an ICT transition.

This ICT fluorescence is advantageous over the fluorescence produced by other coumarin-based derivative compounds including amino or hydroxyl groups. Since the ICT singlet state involves an allowed π-π* transition in an aromatic component, a fluorescence transition probability may be increased. In addition, since this strategy does not rely on the use of heteroatoms with lone-pair electrons, this strategy may obviate dependence of the fluorescence emission on the solvent medium in advance. Facilitated ICT fluorescence is enabled by introducing aromatic units with judiciously controlled oxidation potentials and π-π* transition energies.

In addition, according to the present invention, in order to adjust fluorescence emission of a non-emissive coumarin backbone, an exciplex singlet state may be enabled. An exciplex according to the present invention is an excited-state bimolecular complex formed during excited-state electron transfer. An energy level of the exciplex may be defined by a difference between electrochemical potentials of an electron donor (for example, the semiconducting polymer) and an electron acceptor (for example, the coumarin-based derivative compound), and according to the exemplary embodiment, the exciplex may be formed when the electron-deficient coumarin is embedded in electron-rich polymers such as poly(N-vinylcarbazole) (PVK). Indeed, a positive driving force as large as 0.66 eV was calculated for electron transfer from PVK to the lowest singlet excited state of coumarin.

Photoinduced charge transfer was exploited in PVK films molecularly doped with a series of coumarins as well as in bichromophoric dyads including coumarin and aromatic hydrocarbons, in order to obtain strong fluorescence emission. Through a series of coumarin-based derivative compounds with aryl rings of increasing π conjugation lengths, their ICT and exciplex fluorescence behaviors may be implemented. A photoluminescence quantum yield as high as 0.80 was obtained using the ICT approach, and the exciplex fluorescence behavior enables strong and color-tuned fluorescence emission.

Hereinafter, kinetic Experimental Examples including femtosecond laser flash photolysis experiments and quantum chemical calculations based on time-dependent density functional theory will be described. Experimental Examples were conducted in order to characterize structure-property relationships governing intramolecular and intermolecular charge-transfer fluorescence.

Hereinafter, although the present invention will be described in more detail through Examples of the present invention, the following Examples are provided in order to assist in the understanding of the present invention, but the present invention is not limited thereto.

Example 1

General Synthesis Method

Commercially available chemicals were used as received. All glassware, syringes, and magnetic stir bars were thoroughly dried in a convection oven. Reactions were monitored using thin layer chromatography (TLC) using commercial TLC plates (silica gel 60 F254, Merck Co.). Silica gel column chromatography was performed with silica gel 60 (particle size 0.063-0.200 mm, Merck Co.). $^1H$ and $^{13}C$ NMR spectra were collected using Bruker, Ultrashield 300, 400 and 500 NMR spectrometers and were referred to TMS. High-resolution mass spectra were acquired using JEOL, JMS-600W/JMS-700GC, and Applied Biosystems, Tempo Nano HPLC/QSTAR Elite spectrometers. Elemental analysis was performed using a CE Instrument, EA1110 instrument.

Synthesis of 7-Bromocoumarin

98% $H_2SO_4$ (6.5 mL) was added dropwise to a mixture of 3-bromophenol (5.00 g, 28.9 mmol) and DL-malic acid (2.60 g, 19.4 mmol) at 0° C. The resulting solution was heated at 120° C. for 6 hours. The reaction mixture was poured into crushed ice, and precipitated solids were collected by filtration. The filter cake was washed thoroughly with water in order to remove residual $H_2SO_4$. The solid was dissolved in $CH_2Cl_2$, dried over anhydrous $MgSO_4$, and concentrated under vacuum. A white powder (yield: 34%) was obtained by silica gel column purification ($CH_2Cl_2$:n-hexane=1:1 (v/v)).

$^1H$ NMR (400 MHz, $CDCl_3$) δ: 6.44 (d, J=9.6 Hz, $^1H$), 7.33-7.43 (m, $^2H$), 7.52 (d, J=2.0 Hz, $^1H$), 7.66 (d, J=9.6 Hz, $^1H$). $^{13}C$ NMR (75 MHz, $CDCl_3$) δ: 117.01, 117.90, 120.29, 125.93, 128.02, 128.97, 142.92, 154.40, 160.01.

Synthesis of Phenyl Group-Introduced Coumarin (PC)

7-bromocoumarin (0.300 g, 1.33 mmol), phenylboronic acid (0.195 g, 1.60 mmol), and tetrakis(triphenylphosphine)palladium(0)] (0.077 g, 0.07 mmol) were added into a 100 mL round-bottom flask. The reaction mixture was dissolved in tetrahydrofuran (THF):2 N $K_2CO_3$ (aq.) (2:1, v/v) and refluxed for 2 days. The cooled reaction mixture was poured onto water, and extracted with $CH_2Cl_2$ (100 mL×4 times). An organic layer was dried over anhydrous $MgSO_4$, and concentrated. Silica gel column chromatography was performed while increasing the polarity of the eluents from $CH_2Cl_2$:n-hexane=1:2 (v/v) to $CH_2Cl_2$:n-hexane=1:1 (v/v), thereby obtaining a yellow powder (yield: 52%).

$^1H$ NMR (300 MHz, $CDCl_3$) δ: 6.44 (d, J=9.5 Hz, $^1H$), 7.42-7.56 (m, 6H), 7.62-7.65 (m, 2H), 7.75 (d, J=9.5 Hz, $^1H$). $^{13}C$ NMR (126 MHz, $CDCl_3$) δ: 115.26, 116.54, 118.02, 123.53, 127.43, 128.33, 128.75, 129.29, 139.38, 143.25, 145.29, 154.73, 161.01. HR MS ($FAB^+$, m-NBA): Calcd for $C_{15}H_{10}O_2$ ($[M+H]^+$), 223.0759; found, 223.0765. Anal. Calcd for $C_{15}H_{10}O_2$: C, 81.07; H, 4.54. Found: C, 81.02; H, 4.51.

Example 2

Synthesis of 1-Naphthyl Group-Introduced Coumarin (NC)

The same procedure was performed as in Example 1 except for using 1-naphthylboronic acid instead of phenylboronic acid. The NC was obtained as a white solid (yield: 85%).

$^1H$ NMR (400 MHz, $CDCl_3$) δ: 6.48 (d, J=9.6 Hz, $^1H$), 7.43-7.57 (m, 6H), 7.60 (d, J=8.0 Hz, $^1H$), 7.80 (d, J=9.6 Hz, $^1H$), 7.86 (d, J=8.4 Hz, $^1H$), 7.93 (t, J=6.4 Hz, $^2H$). $^{13}C$ NMR (126 MHz, $CDCl_3$) δ: 116.78, 118.07, 118.43, 125.53, 126.30, 126.67, 126.76, 127.29, 127.79, 128.70, 128.85, 131.27, 134.03, 138.39, 143.34, 145.14, 154.27, 160.97. HR MS ($FAB^+$, m-NBA): Calcd for $C_{19}H_{12}O_2$ ($[M+H]^+$), 273.0916; found, 273.0914. Anal. Calcd for $O_{19}H_{12}O_2$: C, 83.81; H, 4.44. Found: C, 83.81; H, 4.44.

Example 3

Synthesis of 9-Anthryl Group-Introduced Coumarin (AC)

The same procedure was performed as in Example 1 except for using 9-anthrylboronic acid instead of phenylboronic acid. The AC was obtained as a yellow powder (yield: 28%). $^1H$ NMR (300 MHz, $CDCl_3$) δ: 6.55 (d, J=9.6 Hz, $^1H$), 7.35-7.41 (m, 3H), 7.46-7.51 (m, 3H), 7.59-7.62 (m, $^2H$), 7.70 (d, J=7.5 Hz, $^1H$), 7.88 (d, J=9.6 Hz, $^1H$), 8.08 (d, J=8.4 Hz, $^2H$), 8.56 (s, $^1H$). $^{13}C$ NMR (126 MHz, $CDCl_3$) δ: 117.00, 118.31, 119.79, 125.43, 126.12, 126.17, 127.68, 127.93, 128.69, 129.96, 131.40, 134.62, 143.40, 143.44, 154.29, 160.87. HR MS ($FAB^+$, m-NBA): Calcd for $C_{26}H_{14}O_2$ ($[M+H]^+$), 323.1072; found, 323.1072. Anal. Calcd for $C_{23}H_{14}O_2$: C, 85.70; H, 4.38. Found: C, 85.70; H, 4.40.

Experimental Example 1

STEADY-State UV-Vis Absorption Measurement

UV-vis absorption spectra were measured using an Agilent, Cary 300 spectrophotometer at 298 K. 10 μM or 50 μM solutions were freshly prepared prior to collecting the measurement values. Polymer films were spin-coated onto quartz plates (1 cm×1 cm), using an EPLEX, SPIN-1200D spin coater. 1,2-Dichloroethane solutions containing 10 wt % poly(N-vinylcarbazole) (PVK) or poly(methyl methacrylate) (PMMA) and coumarin-based derivative compounds (10 wt % with respect to the polymer) were sonicated for 30 minutes or more. The polymer solution was passed through a membrane filter (pore size: 8.0 μm) in order to remove insoluble particles.

Experimental Example 2

Steady-State Photoluminescence Measurement

Photoluminescence spectra were measured using a PTI, Quanta Master 400 scanning spectrometer at 298 K. The 10 μM solutions or the polymer films containing 10 wt % dopants were used for the measurement. Relative photoluminescence quantum yields (PLQYs) of the solutions were determined according to the following standard equation: $PLQY=PLQY_{ref}\times(I/I_{ref})\times(A_{ref}/A)\times(n/n_{ref})^2$, where A, I, and n are absorbance at an excitation wavelength, integrated photoluminescence intensity, and a refractive index of a solvent, respectively. 9,10-Diphenylanthracene in toluene solution was used as an external reference ($PLQY_{ref}=1.00$). The PLQY values of the polymer films were determined by integrating over a sphere (PTI), according to the manufacturer's protocol.

Experimental Example 3

Photoluminescence Lifetime Measurement

50 μM solutions in Ar-saturated cyclohexane and polymer films doped with 10 wt % coumarin-based derivative compounds were used to determine the photoluminescence lifetimes of the coumarin-based derivative compounds. Photoluminescence decay traces were acquired using time-correlated single-photon-counting (TCSPC) techniques using a PicoQuant, FluoTime 200 instrument after picosecond pulsed laser excitation. A 377 nm diode laser (Pico- Quant, Germany) was used as the excitation source. Photoluminescence signals were collected through an automated motorized monochromator. Photoluminescence decay profiles were analyzed using single or multi exponential decay models (OriginPro 8.0, OriginLab).

Experimental Example 4

Cyclic Voltammetry

Cyclic voltammograms of the deaerated $CH_3CN$ solutions (3 mL) containing 2.0 mM coumarin-based derivative compounds and 0.10 M $TBAPF_6$ supporting electrolyte were collected at 298 K using a CHI630B instrument (CH Instruments). A conventional three-electrode cell was used with a platinum working electrode and a platinum wire as a counter electrode. The potentials were recorded with respect to an $Ag/AgNO_3$ (0.010 M) pseudo reference electrode and were adjusted to values corresponding to a saturated calomel electrode (SCE) by adding 0.29 V. A scan rate was 0.10 V/s.

Experimental Example 5

Differential Pulse Voltammetry

Differential pulse voltammograms of the deaerated $CH_3CN$ solutions (3 mL) containing 2.0 mM coumarin-based derivative compounds and 0.10 M $TBAPF_6$ supporting electrolyte were measured at 298 K using a CHI630B instrument (CH Instruments). A conventional three-electrode cell was used with a platinum working electrode and a platinum wire as a counter electrode. The potentials were recorded with respect to an $Ag/AgNO_3$ (0.010 M) pseudo reference electrode and were adjusted to values corresponding to SCE by adding 0.29 V. A scan rate was 4.0 mV/s.

Experimental Example 6

DFT/TD-DFT Calculation

Quantum chemical calculations based on density functional theory (DFT) were carried out using the Gaussian 09 program. Geometry optimization and single point calculation of model structures were performed using a long range corrected version of B3LYP using the Coulomb-attenuating method (CAM-B3LYP) and the 6-311+G(d,p) basis set. The polarizable continuum model (CPCM), parameterized for THF, was applied during the geometry optimization step. Frequency calculation was performed in order to assess stability of convergence. Time-dependent-density functional theory (TD-DFT) calculation was applied to the optimized geometries using the same functionals and basis sets that were used for geometry optimization. The polarizable continuum model (CPCM) parameterized for THF was applied to account for solvation effects. The twenty lowest singlet and triplet states were calculated and analyzed.

Experimental Example 7

Femtosecond Laser Flash Photolysis

Femtosecond transient absorption spectroscopy experiments were conducted using an ultra-fast source, Integra-C (Quantronix Corp.), an optical parametric amplifier, TOPAS (Light Conversion Ltd), and a commercially available optical detection system, Helios, provided by Ultrafast Systems LLC. The source of the pump and probe pulses was the fundamental output of Integra-C (780 nm, 2 mJ per pulse and FWHM=130 fs) at a repetition rate of 1 kHz. A 75% portion of the fundamental output of the laser was introduced into TOPAS, which includes optical frequency mixers capable of turning the output over the range 285-1660 nm. The rest of the output was used to generate white light. Prior to generating the probe continuum, a variable neutral density (ND) filter was inserted into the path in order to obtain a stable continuum, and the laser pulse was fed to a delay line that provided an experimental time window of 3.2 ns with a maximum step resolution of 7 fs. An excitation wavelength of 350 nm in the TOPAS output was selected as a pump beam. since this TOPAS output consisted of the desired wavelength as well as the other unnecessary wavelengths, the latter were deflected using a wedge prism with a wedge angle of 18°. The desired beam was used to irradiate a sample film with a spot size of 1 mm diameter. The beam merged with a white probe pulse at small angles (<10°). After passing through the film, the probe beam was focused onto a fiber optic cable connected to a charge-coupled device (CCD) spectrometer in order to record the time-resolved spectra (470-800 nm). Typically, 3000 excitation pulses were averaged over 3 seconds in order to obtain a transient spectrum at a set delay time. Kinetic traces at appropriate wavelengths were assembled from the time-resolved spectral data. All measurements were conducted at room temperature, 298 K.

Molecular Design and Synthesis

Figure 2:
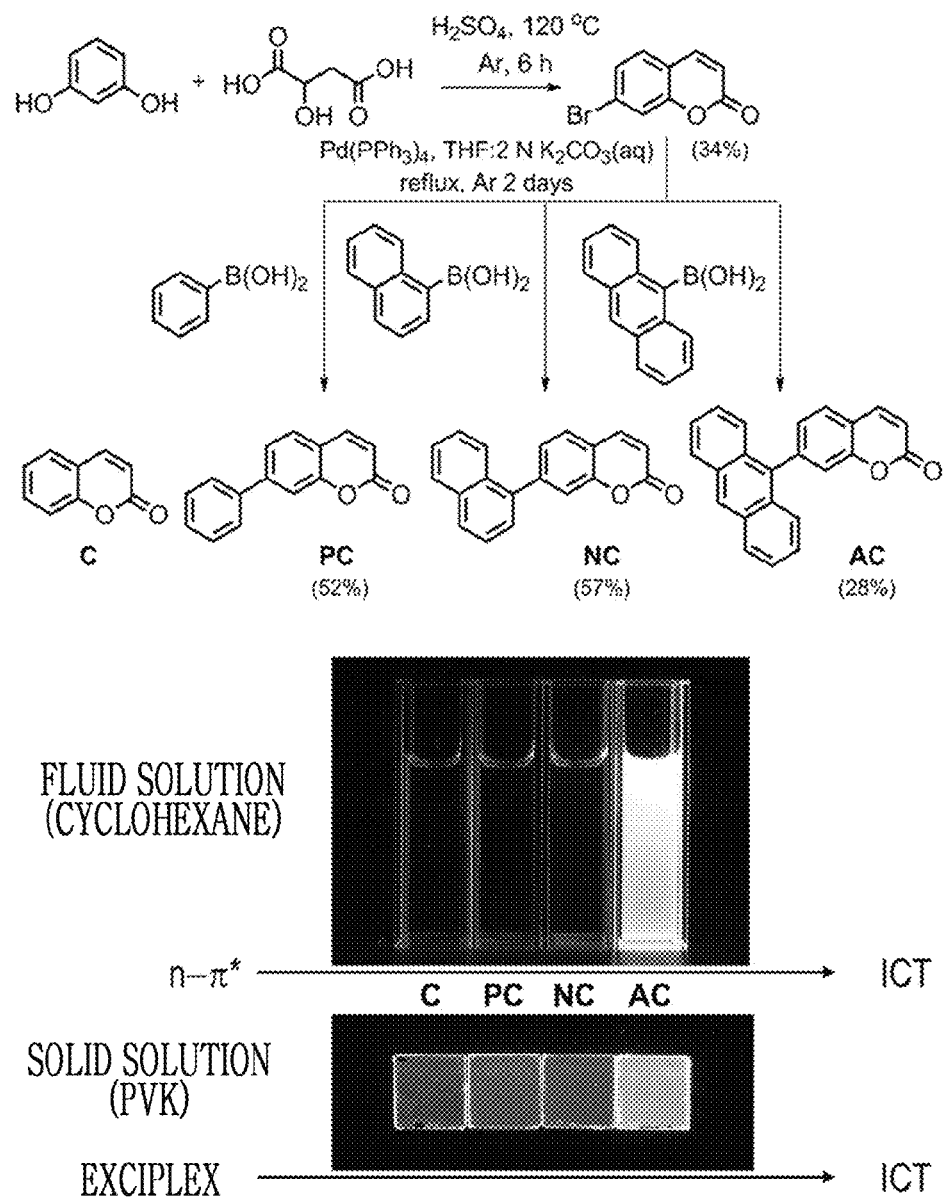
FIG. 2 is a schematic view illustrating synthesis and fluorescence emission characteristics of a coumarin compound in the exemplary embodiment of the present invention.

FIG. 2 illustrates chemical structures of the coumarin molecules examined in the present invention. A series of coumarin-based derivative compounds were designed to incorporate aryl rings with increasing π-conjugation lengths. Phenyl (PC), 1-naphthyl (NC), and 9-anthryl (AC) moieties were introduced at the 7-position of 1-benzopyran-2-one (C). Structural control was used to precisely adjust electrochemical potentials of the obtained bichromophoric coumarins. Specifically, variations in the aryl groups decreased the ground-state oxidation potential (E") in the following order: C>PC>NC>AC, without significantly altering the ground-state reduction potential ($E_{red}$) of the coumarin-based derivative compounds. As a result, the ICT transition state energy, which was primarily estimated based on $E_{ox}$–$E_{red}$, decreased from PC to AC. This energetic shift eventually situated the ICT transition state below the non-fluorescent n-π* transition state, thereby activating a fluorescence channel. That is, as described above, the ICT singlet state may be located below an n-π* singlet state depending on oxidation potentials of aromatic units, thereby activating the fluorescence channel. Aromatic hydrocarbons having extended π conjugation may promote ICT transition.

Figure 3:
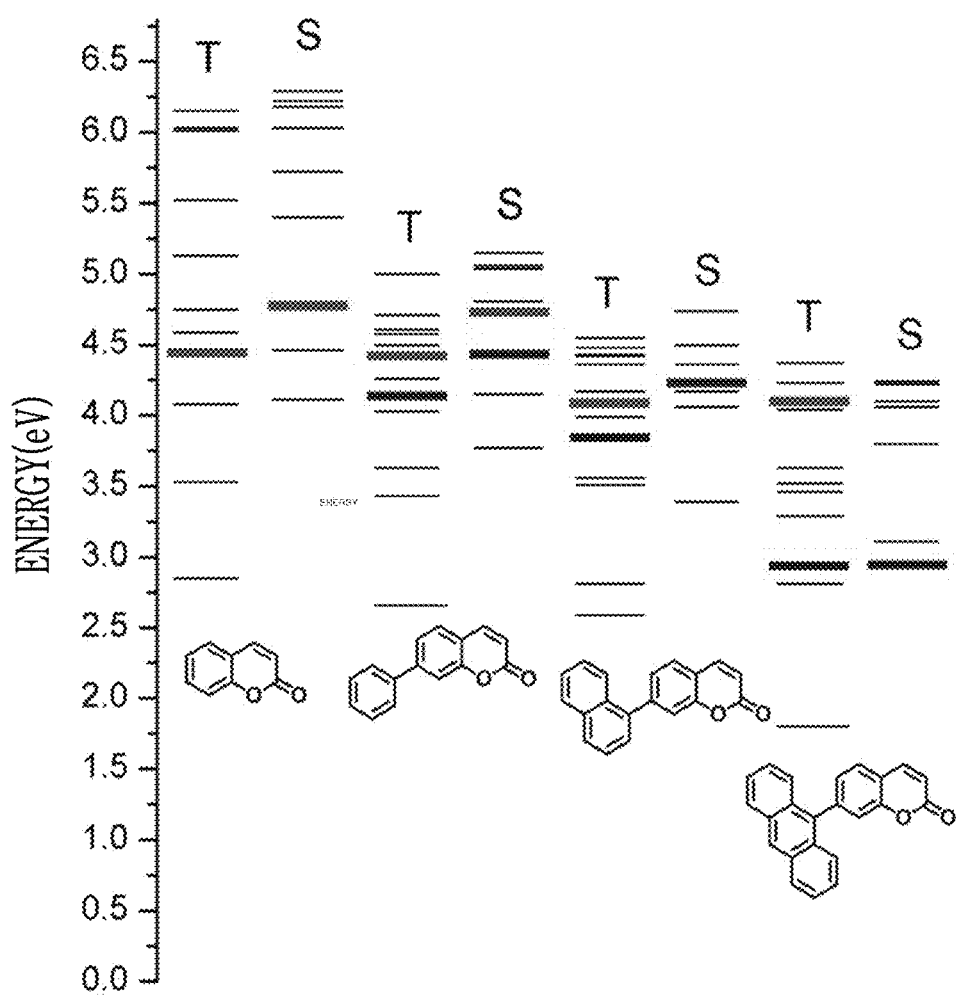
FIG. 3 illustrates calculated [CAM-B3LYP/6-311+G(d,p)//TD-CAM-B3LYP/6-311+G(d,p):CPCM(THF)] energy of singlet (S) and triplet (T) excited states of the coumarin compound in the exemplary embodiment of the present invention.

Synthetic control over the excited states was designed based on quantum chemical calculation using time-dependent density functional theory (TD-DFT, CAM-B3LYP/6-311+G(d,p)//TD-CAM-B3LYP/6-311+G(d,p):CPCM (THF)). Twenty singlet and triplet states were modeled, and their electronic energies are illustrated in FIG. 3. FIG. 3 illustrates calculated [CAM-B3LYP/6-311+G(d,p)//TD-CAM-B3LYP/6-311+G(d,p): CPCM(THF)] energy of singlet (S) and triplet (T) excited states of the coumarin compound. In FIG. 3, red and blue bars illustrate n-π* and ICT transition states, respectively. The lowest singlet states (Si) were predicted to predominantly possess π-π* character, except for AC, which is due to the use of a conductor-like polarizable continuum model (CPCM) parameterized for polar THF. Orthogonal disposition of the aryl ring and the coumarin plane disrupted conjugation across the entire molecule and localized the π-π* transition within the coumarin moiety. Interestingly, increased π conjugation in the aryl ring increased the singlet n-π* transition energy, which may be due to stabilization of a non-bonding orbital on a carbonyl group. In contrast, the ICT transition energy decreased depending on the conjugation length. This behavior persisted across the series of coumarins and eventually basically, the lowest singlet state in AC was predominantly ICT.

Control over the aryl group was intimately linked to the formation of the exciplex. Since the excited-state reduction potential ($E_{red}$*) was calculated as $E_{red}$-band gap energy, change of the aryl groups from phenyl (PC) to 9-anthryl (AC) led to a cathodic shift in $E_{red}$*. The driving force for electron transfer from PVK to the excited-state coumarin-based derivative compounds ($\Delta G_{eT}$) was calculated using $-\Delta G_{eT} = -e \cdot [E_{ox}(PVK) - E_{red}*(coumarin)]$. Therefore, AC, which was characterized by the smallest $E_{red}*$, was expected to be least predisposed to exciplex formation, whereas C, characterized by the largest band gap energy (i.e., the largest $E_{red}*$), favored exciplex formation.

The molecules were synthesized through a two-step procedure including a Pechmann condensation of m-bromophenol and malic acid, followed by Pd(0)-catalyzed Suzuki-Miyaura coupling using commercially available aryl boronic acid. The purified compounds were characterized by multinuclear NMR spectroscopy, high-resolution mass spectrometry, and elemental analysis. The characterization analysis data were fully consistent with the proposed structures.

Fluorescence Turn-on by Intramolecular Charge Transfer

With the exception of AC, the coumarin-based derivative compounds were minimally fluorescent in cyclohexane solutions at 298 K. The observation as described above was consistent with the calculated predictions and previous studies, which suggested that a non-radiative n-π* transition provided the dominant channel for excited-state relaxation in non-polar solvents. Indeed, the photoluminescence quantum yield (PLQY, 9,10-diphenylanthracene standard) was as low as 0.005 for C. The PLQY value increased in proportion to the conjugation length of the aryl ring (Table 1). In addition, it was confirmed that differences between oxidation potential ($E_{ox}$) values and reduction potential ($E_{red}$) values of the coumarin-based derivative compounds were larger than energy of emitted fluorescence ($E_{ems}$). From the energy relationship as described above, it may be appreciated that ICT transition was observed in the non-emissive n-π* singlet state. Further, Table 1 illustrates photophysical and electrochemical data obtained from the coumarin-based derivative compounds in fluid and solid solution states. An identical behavior was found in the photoluminescence lifetimes ($t_{obs}$) recorded at the photoluminescence peak wavelengths after picosecond pulsed photoexcitation at 377 nm (Table 1). $t_{obs}$ increased from 0.098 ns for C to 2.8 ns for AC. The increase as described above was ascribed to the diminished influence of the non-emissive n-π* transition, as predicted by the TD-DFT calculations. The non-radiative rates [$k_{nr}$, $k_{nr}=(1-PLQY)/t_{obs}$] decreased as the number of fused phenyl rings in the aryl groups increased: C, $1.0 \times 10^{10}$ s$^{-1}$; PC, $8.2 \times 10^9$ s$^{-1}$, NC, $2.6 \times 10^9$ s$^{-1}$; AC, $7.1 \times 10^7$ s$^{-1}$.

Figure 4:
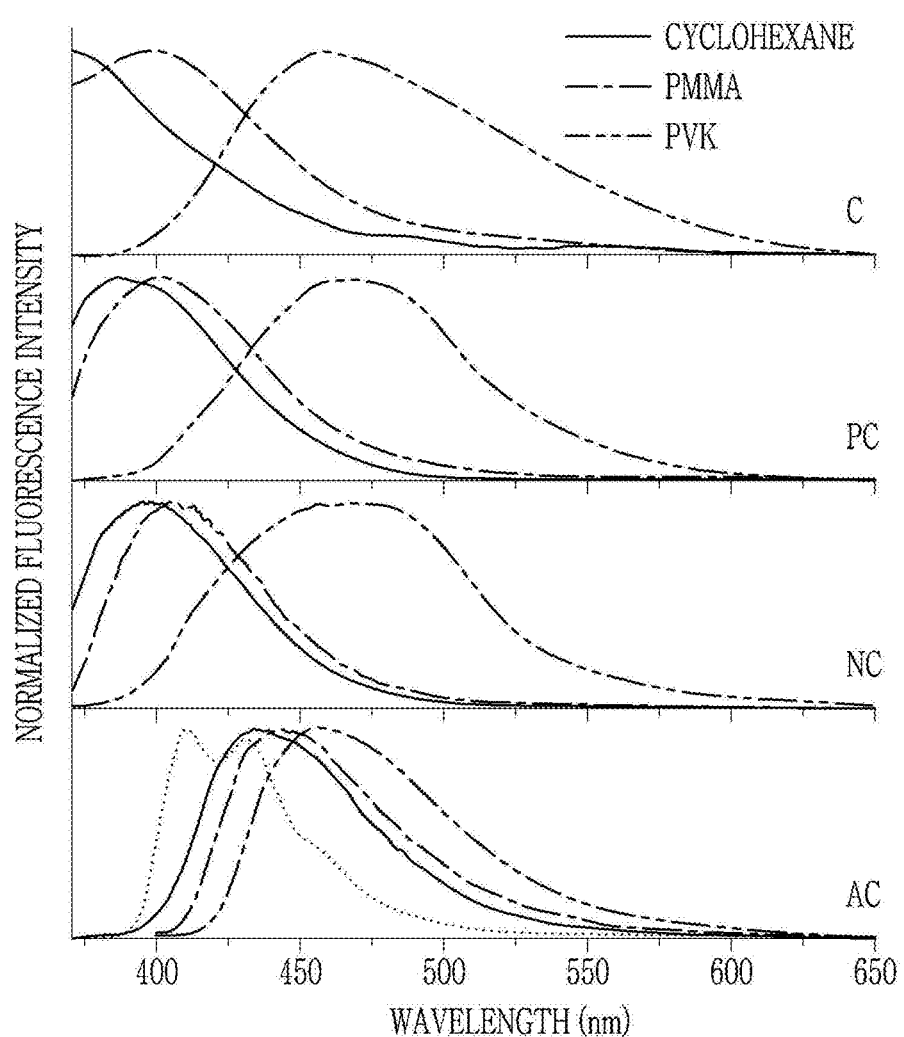
FIG. 4 is a graph illustrating photoluminescence spectra of the coumarin-based derivative compounds in fluid (10 μM in cyclohexane (black)) or solid (10 wt % in PMMA (blue) and PVK (red)) solutions in the exemplary embodiment of the present invention.

The fluorescence properties of AC differed markedly from those of the other coumarin-based derivative compounds. The photoluminescence emission spectrum exhibited a large 2300 cm$^{-1}$ bathochromic shift relative to the spectra of the other coumarin-based derivative compounds (FIG. 4). FIG. 4 is a graph illustrating photoluminescence spectra of the coumarin-based derivative compounds in fluid (10 μM in cyclohexane (black)) or solid (10 wt % in PMMA (blue) and PVK (red)) solutions, and a photoluminescence spectrum of 9,10-diphenylanthracene was illustrated for comparison (dotted black curve). The spectral profile of AC was broad, unlike the vibronically resolved fluorescence spectrum of 9,10-diphenylanthracene. These characteristics suggested that an ICT transition was responsible for the observed fluorescence of AC. Strong solvatochromism, as demonstrated by the Lippert-Mataga plot, corroborated this hypothesis. Cyclic and differential pulse voltammetry measurements revealed a cathodic shift in the oxidation potential of AC ($E_{ox}$=1.24 V vs. SCE) relative to the $E_{ox}$ values (1.60-2.27 V vs. SCE) of the other coumarin-based derivative compounds (Table 1), which may further support the presence of ICT fluorescence. The ICT fluorescence was very bright, with a PLQY as high as 0.80. Indeed, the $k_{nr}$ value ($7.1 \times 10^7$ s$^{-1}$) was two orders of magnitude smaller than the values obtained for other coumarins. Taken together, these results demonstrated that the incorporation of anthracene boosted the fluorescence intensity by activating an ICT transition.

TABLE 1

| | Fluid Solution | | | | | | | | Solid Solution[a] | | |
|---|---|---|---|---|---|---|---|---|---|---|---|
| | λabs (nm; ε, $10^4$ m$^{-1}$ cm$^{-1}$)b | ΔET (eV) | Eox (eV, V vs SCE)[e] | Ered (Ev, V vs SCE)[e] | λems (nm)[b] | Eems eV | PLOY bf | $t_{obs}$ (ns)[g] | $\lambda_{ems}$ (nm) | PLQY[h] | $T_{avg}$ |
| C | 311(0.53) | 2.73[c] | 2.27 | -1.75 | 388 | 3.19 | 0.005 | 0.098 | 458 | 0.06 ± 0.002 | 23 |
| PC | 327(1.57) | 2.55[d] | 1.86 | -1.66 | 396 | 3.13 | 0.012 | 0.12 | 469 | 0.05 ± 0.002 | 24 |
| NC | 327(1.50) | 2.55[d] | 1.60 | -1.68 | 402 | 3.08 | 0.081 | 0.36 | 468 | 0.04 ± 0.01 | 24 |
| AC | 385(0.61) | N.A | 1.24 | -1.67 | 444 | 2.79 | 0.80 | 2.8 | 457 | 0.18 ± 0.006 | 3.1 |

[a]10 wt % in PVK, 298K.
[b]10 μM in cyclohexane solutions, 298K.
[c]50 mM in 2-MeTHF, 78K.
[d]50 μM in iodoethane, 78K.
[e]Determined by cyclic and differential pulse voltammetry using 2.0 mM CH$_3$CN solutions containing 0.10M TBAPF$_6$. Pt working and counter electrodes, and an Ag/AgNO$_3$ pseudo reference electrode were employed. Scan rate = 0.10 V s$^{-1}$ (cyclic voltammetry) and 4.0 mV s$^{-1}$ (differential pulse voltammetry).
[f]Photoluminescence quantum yields were determined relative to that of a 9,10-diphenylanthracene standard (solvent, PLQY = 1.00).
[g]Photoluminescence decay traces for 50 μM coumarin-based derivative compounds in Ar-saturated toluene solutions or PVK films doped with 10 wt % coumarin-based derivative compounds were monitored at the emission maximum after picosecond pulsed laser excitation at 377 nm.
[g]The photoluminescence lifetime ($T_{obs}$) values determined through nonlinear least-squares fits to monoexponential (cyclohexane solutions) or triexponential (PVK films) decay models. The weighted average lifetime ($t_{avg}$) of the triexponential decay traces was calculated using $t_{avg}$ = ($\Sigma a_i \cdot t_i^2$)/($\Sigma a_i \cdot t_i$) (i = 1–3), where $a_i$ and $T_i$ are the pre-exponential factor and the time constant, respectively.
[h]Photoluminescence quantum yields were determined absolutely by integrating over a sphere. The measurements were performed in triplicate.

Fluorescence Turn-on by Exciplex Formation

The non-fluorescent coumarin-based derivative compounds, C, PC, and NC, became emissive when they were doped into PVK at 10 wt % (FIG. 2). As illustrated in FIG. 4, the fluorescence peak wavelengths ($l_{ems}$) exhibited bathochromic shifts of 3500-3900 cm$^{-1}$ relative to the solution spectra. The shifts did not result from planarization of π systems in the solid state because much smaller bathochromic shifts of 300 to 700 cm$^{-1}$ were observed in poly(methyl methacrylate) (PMMA) films doped with C, PC, or NC at the same doping concentrations (10 wt %). The PLQY values determined absolutely by integrating over a sphere were 0.02, 0.05, and 0.04 for C, PC, and NC, respectively. These values were one order of magnitude larger than the PLQY values obtained in cyclohexane solutions. By contrast, the PLQY values of the PMMA films containing 10 wt % coumarin-based derivative compounds were relatively low: C, 0; PC, 0.019; and NC, 0.027, which indicates that solidification did not significantly contribute to the fluorescence observed in the PVK films.

Figure 5:
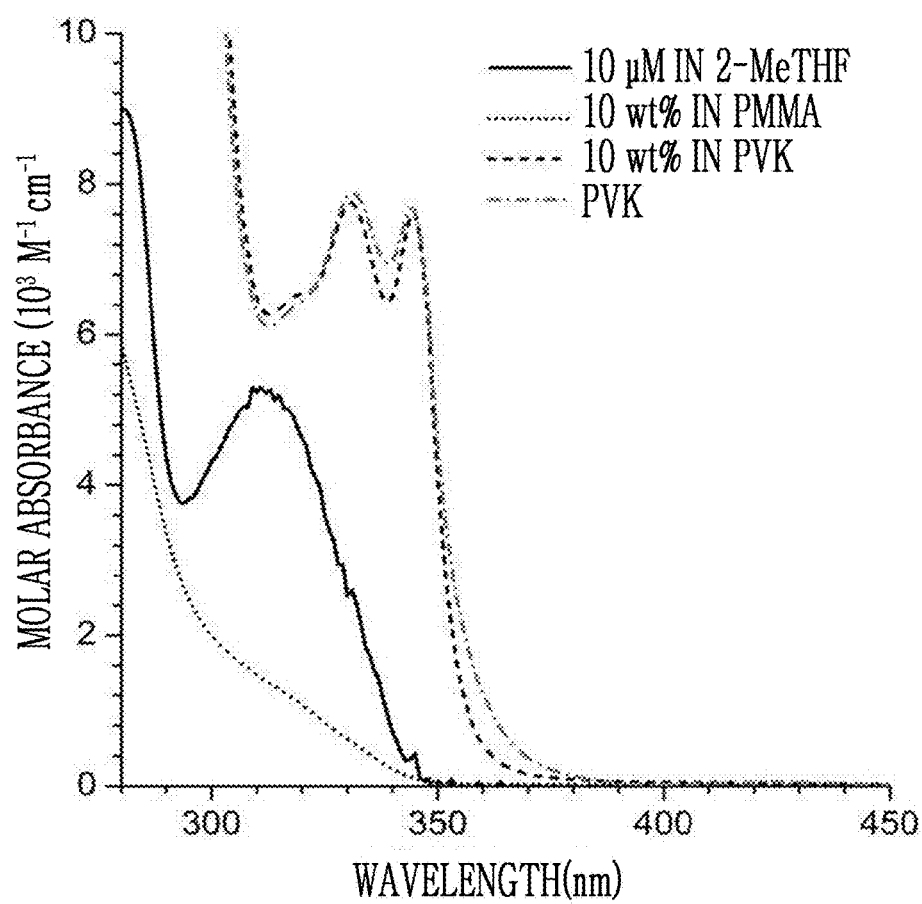
FIG. 5 is a graph illustrating UV-vis absorption spectra of C measured in fluid (10 μM in 2-MeTHF (solid black line)) or solid (10 wt % in PMMA (dotted grey line) or PVK (dashed black line)) solutions in the exemplary embodiment of the present invention.

The $l_{ems}$ and PLQY values obtained from the PVK films were compared with those obtained from the cyclohexane solutions and from PMMA films, and as a result, it was confirmed that the fluorescence emission did not originate from an excitonic state (a π-π* transition state or an ICT transition state) in the coumarin-based derivative compounds. The photoluminescence peak wavelengths varied continuously with the difference between $E_{ox}$(PVK)(1.18 V vs SCE) and the ground-state reduction potential ($E_{red}$; C, −1.75 V; PC, −1.66 V; NC, −1.68 V vs SCE) of the coumarin-based derivative compounds (Table 1). The UV-vis absorption spectrum of C in the 2-MeTHF solution (10 μM) was compared with the spectra obtained from the PMMA (10 wt %) and PVK (10 wt %) solid solutions in order to reveal the absence of ground-state charge-transfer interactions between the coumarin-based derivative compounds and PVK (FIG. 5). FIG. 5 is a graph illustrating UV-vis absorption spectra of C measured in fluid (10 μM in 2-MeTHF (solid black line)) or solid (10 wt % in PMMA (dotted grey line) or PVK (dashed black line)) solutions, and the absorption spectrum of the PVK (dashed grey line) was included for comparison.

Figure 6:
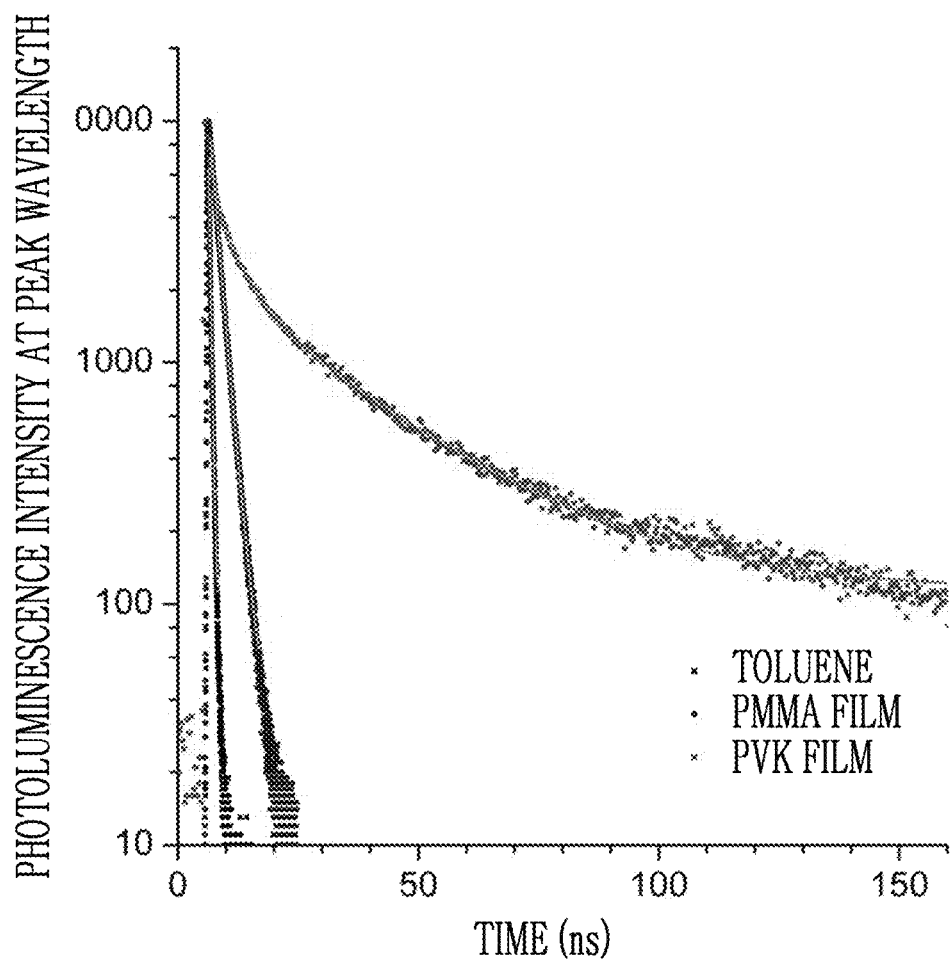
FIG. 6 is a graph illustrating photoluminescence decay traces of NC after picosecond pulsed laser excitation at 377 nm (pulse duration=8 ns) in the exemplary embodiment of the present invention.
Figure 7A:
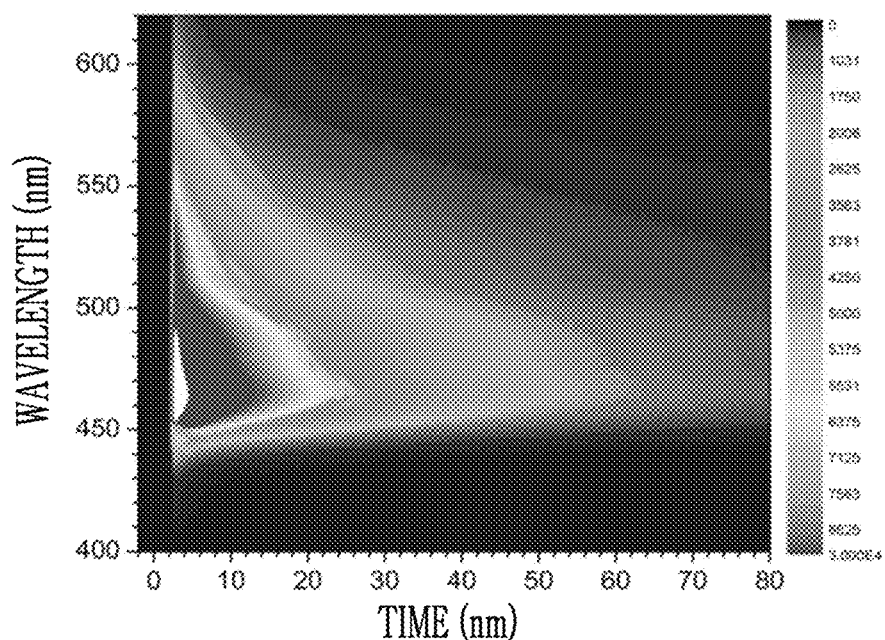
FIG. 7A illustrates time-resolved photoluminescence spectra of PVK films doped with 10 wt % PC and FIG. 7B illustrates time-resolved photoluminescence spectra of PVK films doped with 10 wt % AC after picosecond pulsed laser excitation at 377 nm in the exemplary embodiment of the present invention.
Figure 7B:
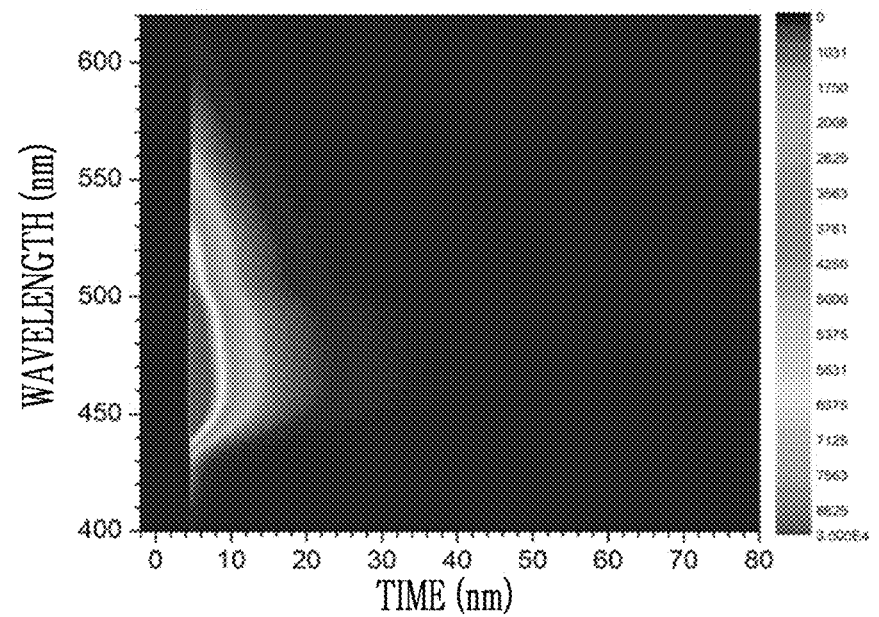

In order to gain additional information on the nature of the fluorescence emission, photoluminescence decays were monitored for the coumarin-doped (10 wt %) PVK films at the emission peak wavelengths after picosecond pulsed laser photoexcitation at 377 nm. The decay trace of a PVK film containing NC exhibited a biexponential decay behavior (FIG. 6). FIG. 6 illustrates photoluminescence decay traces of NC after picosecond pulsed laser excitation at 377 nm (pulse duration=8 ps): black, 50 μM in an Ar-saturated toluene solution; blue, 10 wt % in a PMMA film; and red, 10 wt % in a PVK film. The grey curves are non-linear least squares fits to monoexponential (black and blue) and biexponential (red) decay models. This multiphasic decay markedly differed from those of NC in a fluid solution (50 μM in Ar-saturated toluene) and a PMMA film (10 wt %), which adhered to a monoexponential decay model with $t_{obs}$ values in the subnanosecond ranges. A weighted average photoluminescence lifetime of the PVK film of NC was 21 ns, being two orders of magnitude longer than that of the solution (0.36 ns; Table 1). The transient photophysical properties were consistent with the previous observations of exciplex fluorescence. The exciplex fluorescence featured several unique properties: 1) prolonged lifetimes of the emissive state, and 2) emission color which was determined by the relative position of electrochemical potentials of individual components (i.e., coumarin and PVK). Inspection of Table 1 reveals that the $t_{obs}$ values of the fluid solutions increased with the π conjugation lengths of the aryl ring (C, 0.098 ns; PC, 0.12 ns; NC, 0.36 ns; and AC, 2.8 ns). This observation could be explained on the basis of a decrease in contribution of n-π* transition for the coumarin-based derivative compounds with π-extended rings, as explained earlier. Since emissive exciplex species provided the lowest energy path for excited-state relaxation, an influence of fluorescence quenching n-π* transition was suppressed in PVK. In fact, such non-radiative control yielded the observed behavior in the ratio of PLQY(PVK)/PLQY(cyclohexane). For instance, C with the strong quenching contribution by n-π* transition in fluid solutions showed the largest value for the ratio (12) of PLQY(PVK)/PLQY(cyclohexane). The ratio decreased with the conjugation length of the aryl rings: PC, 4.2; NC, 0.49. In the case of AC, the fluorescence properties were not affected by PVK. The emission peak wavelength of the PVK film (10 wt % doping ratio, 457 nm) did not exhibit a significant bathochromic shift from that (444 nm) of the cyclohexane solution. Similarly, the tubs value (3.1 ns) was nearly identical to that (2.8 ns) obtained in the cyclohexane solution. Time-resolved photoluminescence spectra of PVK films doped with either 10 wt % PC or 10 wt % AC revealed contrasting behaviors (FIG. 7A and FIG. 7B). The retention of the fluorescence properties may be indicative of the absence of the exciplex channel in AC.

Figure 8A:
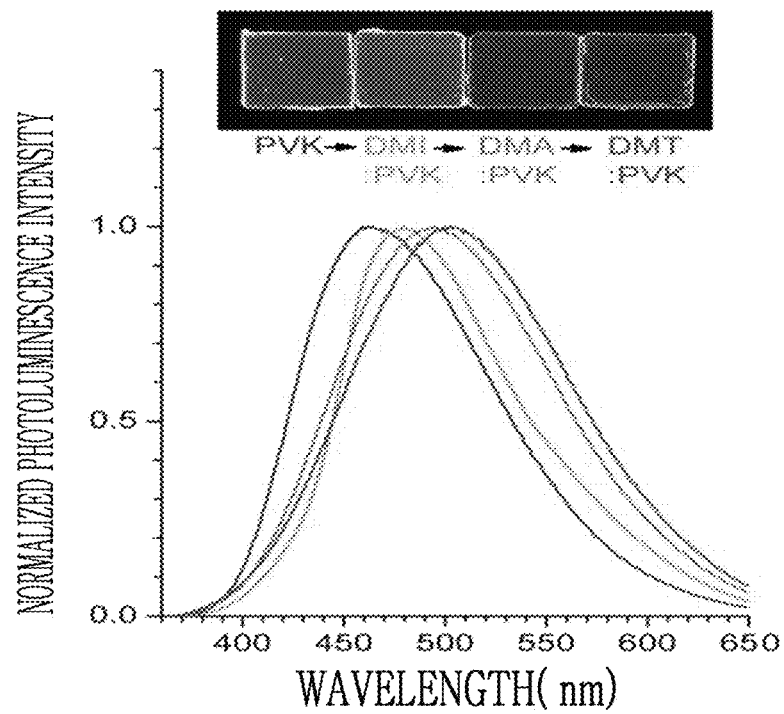
FIG. 8A is a graph illustrating photoluminescence spectra of PVK films doped with 10 wt % C and a 30 wt % electron donor in the exemplary embodiment of the present invention.
Figure 8B:
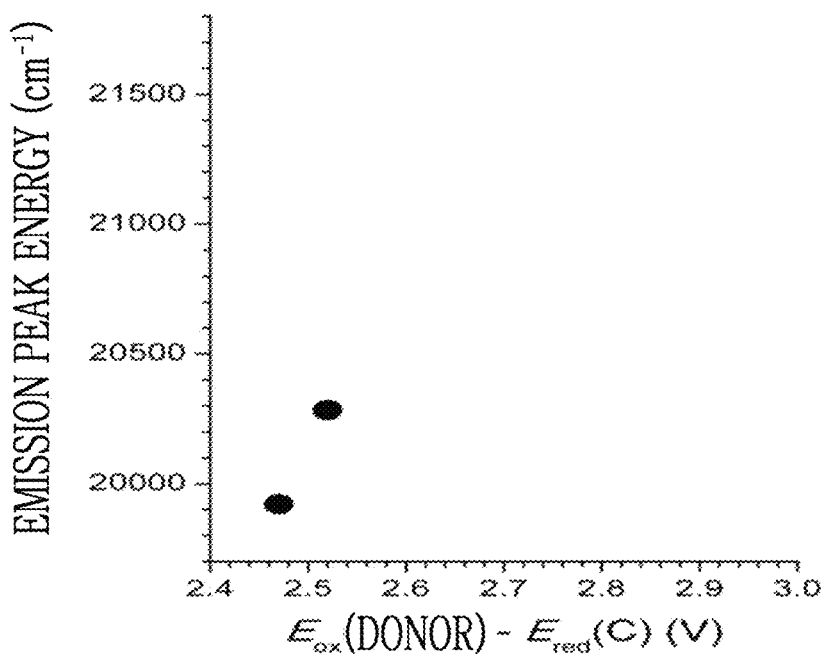
FIG. 8B is a graph illustrating a plot of fluorescence peak wavelength energy and a difference between the ground-state oxidation potentials of the electron donors ($E_{ox}$(donor)) and the ground-state reduction potentials of C ($E_{red}$(C)) in the exemplary embodiment of the present invention.

Fluorescence utility of the exciplex of the coumarin-based derivative compounds was demonstrated by emission color tuning. PVK films containing 10 wt % C were additionally doped with several electron donors (30 wt %) having the $E_{ox}$ values smaller than that of PVK: 1,2-dimethylindole (DMI), 1.06 V; N,N-dimethylaniline (DMA), 0.77 V; and N,N-dimethyl-p-toluidine (DMT), 0.72 V (all potentials are vs. SCE). FIG. 8A is a graph illustrating photoluminescence spectra of PVK films doped with 10 wt % C and a 30 wt % electron donor. Electron donors: 1,2-dimethylindole (DMI), N,N-dimethylaniline (DMA); and N,N-dimethyl-p-toluidine (DMT). The inset photograph of FIG. 8A illustrates the fluorescence emission of the PVK films of 10 wt % C in the absence (far left) and presence of DMI, DMA, and DMT (from the second left). As illustrated in FIG. 8A, the exciplex fluorescence emission of the ternary mixtures shifted bathochromically with decreasing $E_{ox}$ of the electron donors. Indeed, the fluorescence peak energies exhibited linear proportionality to a difference between an oxidation potential ($E_{ox}$) of the semiconducting polymer and a reduction potential value ($E_{red}$) of the coumarin-based compound [FIG. 8B]. In fact, FIG. 8B is a graph illustrating a plot of the fluorescence peak wavelength energies and the difference between the ground-state oxidation potentials of the electron donors [$E_{ox}$(donor)] and the ground-state reduction potentials of C [$E_{red}$(C)] in Example of the present invention. The photoluminescence decay traces monitored at the emission peak wavelengths followed a triexponential decay model, as seen for the mixture of C and PVK. The weighted average values of the photoluminescence decay were 8.3 ns, 13.8 ns, and 9.2 ns for 1,2-dimethylindole, N,N-dimethylaniline, and N,N-dimethyl-p-toluidine, respectively. These results unambiguously demonstrated that the exciplex is the origin of fluorescence emission, and provided a versatile strategy to adjust fluorescence emission.

Photophysical Monitoring of Excited-State Process

Figure 9:
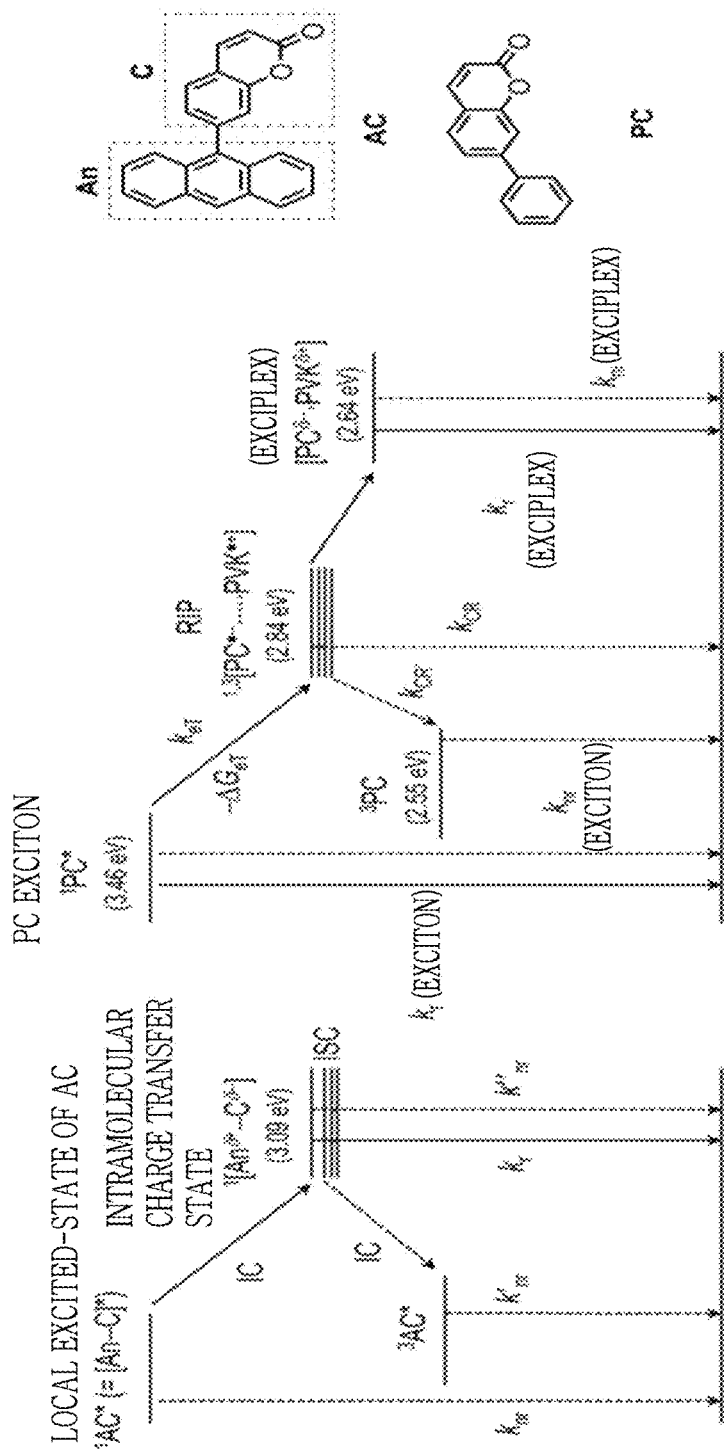
FIG. 9 is a schematic view illustrating a plausible mechanism for the ICT fluorescence of AC, and for generation and relaxation of an exciplex in PVK films doped with PC upon photoexcitation in the exemplary embodiment of the present invention.

Photophysical processes were investigated through the ICT and exciplex emission demonstrated above. FIG. 9 illustrates plausible mechanisms for the photophysical processes in AC (i.e., ICT fluorescence) and PVK films containing PC (i.e., exciplex fluorescence). In both cases, the charge transfer provides fluorescence channels that can harvest the excited-state energy of the n-π*transition state. It should be noted that, without the new channels mediated by charge transfer, the n-π* transition state relaxes to the ground state non-radiatively.

Figure 10A:
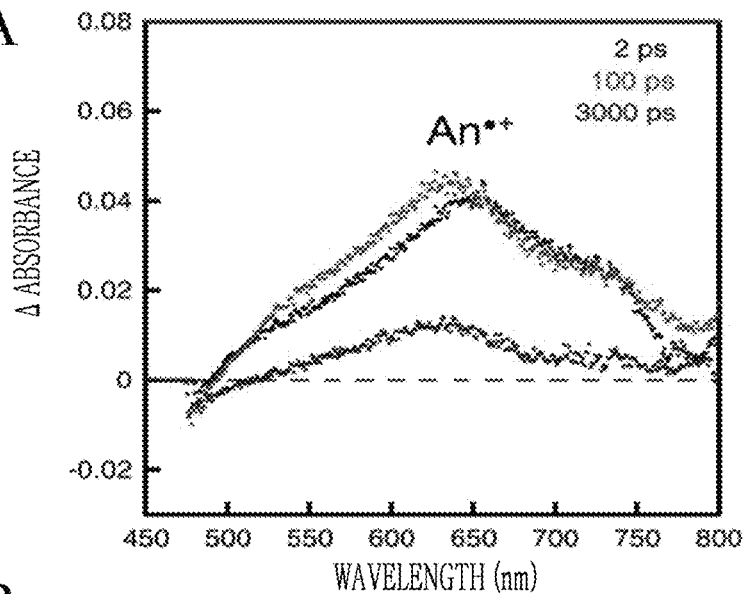
FIG. 10A illustrates transient absorption spectra recorded at 2, 100 and 3000 ps after photoexcitation at 350 nm.
Figure 10B:
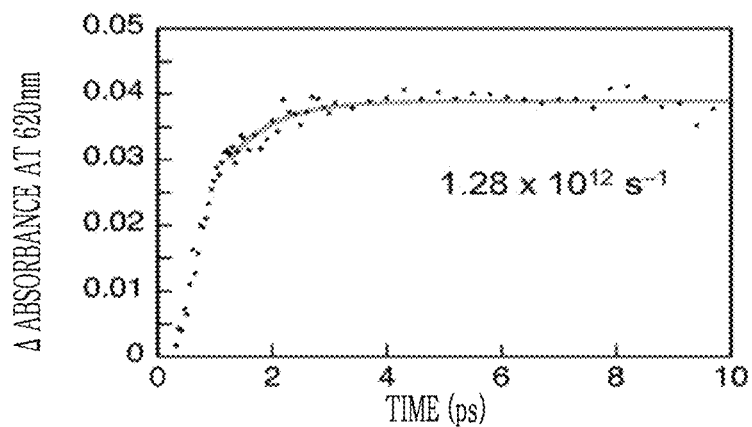
FIG. 10B illustrates rising traces of transient absorption at 620 nm and nonlinear least squares fit.
Figure 10C:
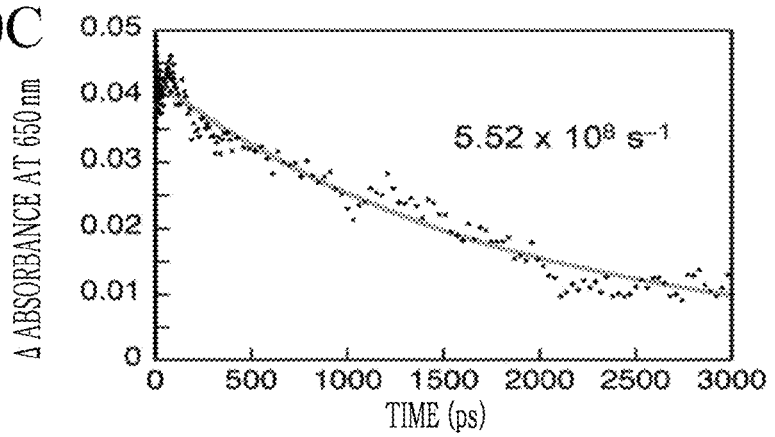
FIG. 10C illustrates decay traces of the transient absorption at 650 nm and the nonlinear least squares fit, during femtosecond laser flash photolysis of a toluene solution of AC (O.D.=0.2 at 350 nm) in the exemplary embodiment of the present invention.

The steady-state and transient photoluminescence results revealed that the ICT transition state is responsible for the fluorescence emission of AC. In order to directly probe the ICT process, femtosecond laser flash photolysis experiments were performed. The transient absorption spectra of toluene solutions of AC (O.D.=0.2 at 350 nm) were acquired after femtosecond pulsed laser photoexcitation at 350 nm. As illustrated in FIG. 10A, a strong absorption band at 630 nm appeared at a rise time of 0.78 ps, and decayed with a time constant of 1.2 ns. The 630 nm band revealed intramolecular formation of a radical cation of anthracene. The rise (0.78 ps) and decay (1.2 ns) times may correspond to the time required for relaxation to the lowest ICT transition and ground states, respectively. The latter time constant was indistinguishable from the photoluminescence lifetime (2.8 ns) of AC recorded in cyclohexane, which further supports this notion. On the contrary, the transient absorption spectra of the other coumarin-based derivative compounds differed from that of AC, and included a transient absorption band at 550 nm. The 550 nm absorption bands were long-lived and did not decay appreciably until 3000 ps.

Figure 11A:
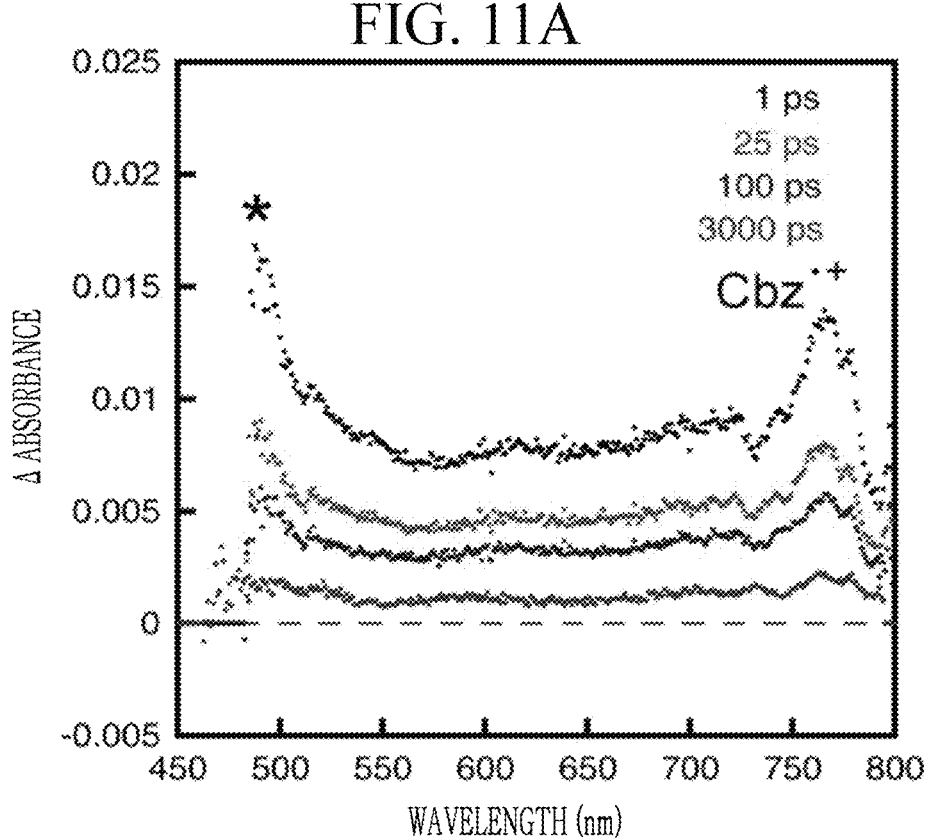
FIG. 11A is a graph illustrating transient absorption spectra recorded at 1, 25, 100, and 1000 ps after photoexcitation at 350 nm.
Figure 11B:
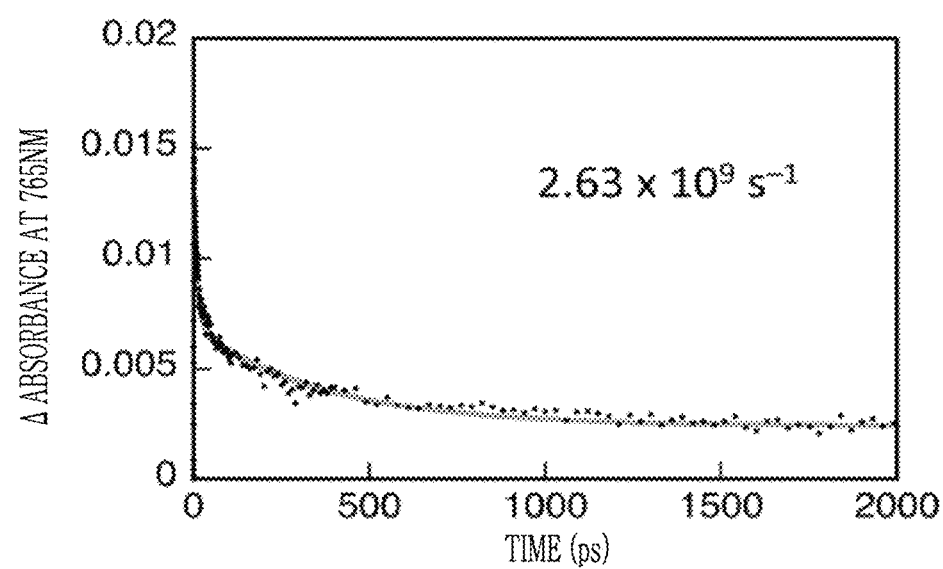
FIG. 11B is a graph illustrating decay traces of transient absorption at 765 nm and a nonlinear least squares, during femtosecond laser flash photolysis of a PVK film doped with 10 wt % PC in the exemplary embodiment of the present invention.

Photoexcitation under UV irradiation (365 nm) produced excited states in both PC (PC*) and PVK (PVK*); however, electron transfer was only allowed from the ground state of PVK to PC* due to a positive driving force of 0.62 eV, which was determined by the difference between the $E_{red}$* of PC and $E_{ox}$ of PVK. Other coumarin-based derivative compounds also displayed a positive driving force for the photoinduced reductive electron transfer to PVK: 0.66 eV(C), 0.57 eV(NC) and 0.24 eV(AC). By contrast, electron transfer from the coumarin-based derivative compound to the excited state of PVK (PVK*) was forbidden due to the negative driving force (−0.10 eV to −0.19 eV). The photoinduced electron transfer produced a radical ion pair ([PC$^{\bullet-}$PVK$^{\bullet+}$]) consisting of a one-electron reduced PC species (PC$^{\bullet-}$) and a one-electron oxidized PVK species (PVK$^{\bullet+}$). In the present Example, it was attempted to determine the rate constant for intermolecular electron transfer using transient photoluminescence techniques by adding N-ethylcarbazole into the coumarin solutions; however, the experiments were hampered by a significant overlap between the fluorescence spectra of N-ethylcarbazole and the coumarin-based derivative compounds. Femtosecond laser flash photolysis revealed an increase in the PVK$^{\bullet+}$ signal within the temporal resolution of the instrument, which indicates the presence of ultra-fast forward electron transfer. Once the [PC$^{\bullet-}$PVK$^{\bullet+}$] has been produced, it underwent charge recombination to produce ground states [CR in FIG. 9B] in PC and PVK or a triplet excited state [CR' in FIG. 9A] in PC. An alternative pathway may involve formation of a fluorescent exciplex. Although the limited spectral resolution impeded discrimination among these three processes, the transient absorption band of PVK$^{\bullet+}$ at 770 nm in PVK films containing 10 wt % PC was detected after femtosecond pulsed laser photoexcitation at 350 nm [FIG. 11A]. A high-energy absorption band at 490 nm corresponded to a triplet transition ($T_1 -> T_n$) in PC. These peak assignments were consistent with those reported previously. Observation of the PVK$^{\bullet+}$ species enabled to trace the decay of [PC$^{\bullet-}$PVK$^{\bullet+}$]. As illustrated in FIG. 11B, the transient absorption of PVK$^{\bullet+}$ exhibited biexponential decay with a weighted average rate [$k_{decay}$(RIP)] of $2.6 \times 10^9$ s$^{-1}$. The $k_{decay}$(RIP) corresponded to a sum of rate constants for charge recombination to the ground state [$k_{CR}$ in FIG. 9B] and the triplet state [$k_{CR'}$ in FIG. 9B] and conversion of the exciplex. The decay rate exceeded the radiative decay rate ($k_r$(exciplex), $2.1 \times 10^6$ s$^{-1}$) and non-radiative decay rate ($k_{nr}$(exciplex), $4.0 \times 10^7$ s$^{-1}$) of the exciplex of PC by three and two orders of magnitudes, respectively (Table 2), which indicates that charge recombination was faster than the relaxation of the exciplex. Table 2 illustrates summary of the rate values characterizing the photophysical processes in the PVK films containing the coumarin-based derivative compounds. Similarly, the $k_{decay}$(RIP) values of C and NC were as large as $0.8 \times 10^9$ s$^{-1}$ and $3.8 \times 10^9$ s$^{-1}$, respectively (Table 2). Unlike the transient absorption spectra of C, PC, and NC compounds, the transient absorption spectrum of PVK films of AC lacked the PVK$^{\bullet+}$ band. This observation indicated that intermolecular electron transfer between PVK and AC was suppressed, despite the positive driving force (0.24 eV), most likely due to the presence of ICT transition.

Figure 12:
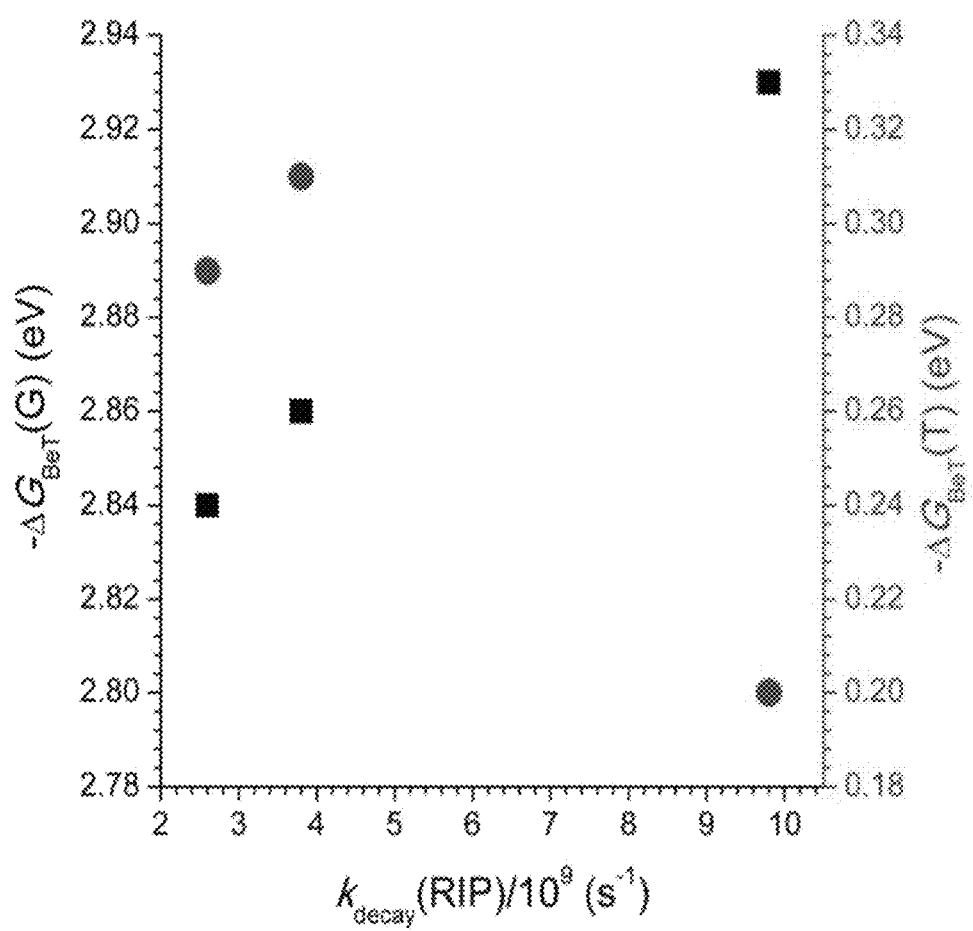
FIG. 12 illustrates plots of driving force for charge recombination within a radical ion pair [PC$^{\bullet-}$-PVK$^{\bullet+}$] to the ground [$-\Delta G_{BeT}(G)$] and triplet [$-\Delta G_{BeT}(T)$] states of the coumarin-based derivative compounds as a function of the rate constant for the decay of the radical ion pair [$k_{decay}$(RIP)].

It should be noted that the decay rates were proportional to the driving force for back electron transfer within the radical ion pair to yield the ground states [$-\Delta G_{BeT}$(G):C, 2.93 eV; PC, 2.84 eV; NC, 2.86 eV]. The $-\Delta G_{BeT}$(G) values were calculated using the relationship, $-\Delta G_{BeT}$(G)=e[$E_{red}$(coumarin)$-E_{OX}$(PVK)], where e is quantity of electric charge of an electron. The driving force for charge recombination to the triplet state of coumarin [$-\Delta G_{BeT}$(T): C, 0.20 eV; PC, 0.29 eV; NC, 0.31 eV] was calculated from the difference between $-\Delta G_{BeT}$(G) and the triplet state energies ($\Delta E_T$) of the coumarin-based derivative compounds. The $\Delta E_T$ values were measured from the low-temperature (78 K) phosphorescence spectra collected from solutions containing 50 μM C in 2-MeTHF or 50 μM PC or NC in iodoethane. As illustrated in FIG. 12, the $k_{decay}$(RIP) was varied linearly with $-\Delta G_{BeT}$(G) but not with $-\Delta G_{BeT}$(T). Taken together, these results suggest that the favored relaxation process for the photo-produced radical ion pair involved non-radiative charge recombination to the ground state, which occurred in the Marcus-normal region of electron transfer.

TABLE 2

| | EXCITON [a] | | EXCIPLEX [b] | | |
|---|---|---|---|---|---|
| | $k_r$ ($10^7$ s$^{-1}$)[d] | $k_{nr}$ ($10^7$ s$^{-1}$)[e] | $k_r$ ($10^7$ s$^{-1}$)[f] | $k_{nr}$ ($10^7$ s$^{-1}$)[g] | $k_{decay}$(RIP) ($10^9$ s$^{-1}$)[c] |
| C | 0 | 14 | 0.26 | 4.1 | 9.8 |
| PC | 0.23 | 12 | 0.21 | 4.0 | 2.6 |
| NC | 14 | 38 | 0.16 | 4.6 | 3.8 |
| AC | 24 | 35 | N.A. | N.A. | N.A. |

[a] 10 wt % in PMMA films, 298 K.
[b] 10 wt % in PVK films, 298 K.
[c] Decay rate of the radical ion pair of PVK and coumarin compound species, determined by laser flash photolysis after femtosecond laser photoexcitation of the PVK films containing 10 wt % coumarin-based derivative compounds at 330 nm (C) and 350 nm (PC, NC, and AC).
[d] Radiative rate constant, $k_r$ = PLQY/$t_{obs}$; PLQY = 0(C), 0.019 ± 0.0008(PC), 0.27 ± 0.007(NC), and 0.41 ± 0.002(AC); $t_{obs}$ = 7.4 ns(C), 8.4 ns(PC), 1.9 ns(NC) and 1.7 ns(AC).
[e] Non-radiative rate constant, $k_{nr}$ = (1 − PLQY)/$t_{obs}$.
[f] Radiative rate constant, $k_r$ = PLQY/$t_{obs}$ see Table 1 for PLQY and $t_{obs}$ values.
[g] Non-radiative speed constant, $k_{nr}$ = (1 − PLQY)/$t_{obs}$.

Since n-π* chromophores undergo fast non-radiative relaxation, the n-π* chromophores are considered to be weak fluorophores. The utility of n-π* fluorophores has not been appreciated, and successful applications of these compounds are scarce, with the exception of coumarin-based derivative compounds including strong electron donors. In the present invention, it was attempt to improve the fluorescence properties of n-π* fluorophores by implementing two photophysical design strategies. These strategies promoted intramolecular and intermolecular charge transfer to electron-deficient n-π* fluorophores, and generated an ICT transition state and an exciplex, both of which were fluorescent. Archetype 1-benzopyran-2-one (coumarin) was chosen as a model platform. Aryl rings including phenyl (PC), 1-naphthyl (NC), and 9-anthryl (AC) were introduced at the 7-position of coumarin. AC was found to display strong ICT fluorescence emission, whereas the fluorescence intensities of coumarin and the other derivatives were very low. The increase in fluorescence was ascribed to the reordering of the electronic states through generation of an ICT transition state and destabilization of the n-π* transition state. The weakly emissive C, PC, and NC became highly fluorescent when doped into PVK films. The fluorescence originated from the exciplex, as demonstrated by the kinetic studies. Femtosecond laser flash photolysis experiments enabled to directly identify the electron-transfer species generated during the exciplex de-excitation processes. The relationship between the electron-transfer rates and the driving force for electron transfer revealed that harmful charge recombination provided the dominant relaxation pathway. This establishment provided valuable insights that further improved the fluorescence properties. Recent studies have described the utility of charge-transfer species as emitting centers, whereas the principles underlying high-efficiency exciplex fluorescence have yet to be fully established. The present inventors hope that the results presented here will provide useful insights into the future utilization of charge-transfer fluorescence.

The above description of the present disclosure is provided for the purpose of illustration, and it would be understood by those skilled in the art that various changes and modifications may be made without changing technical conception and essential features of the present disclosure. Therefore, it is to be understood that exemplary embodiments described hereinabove are illustrative rather than being restrictive in all aspects. For example, each component described to be of a single type can be implemented in a distributed manner. Likewise, components described to be distributed can be implemented in a combined manner.

It is to be understood that the scope of the present invention will be defined by the claims rather than the above-mentioned description and all modifications and alternations derived from the claims and their equivalents are included in the scope of the present invention.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

What is claimed is:

1. A coumarin-based compound represented by the following Chemical Formula 1:

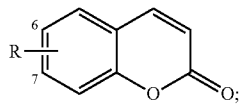

[Chemical Formula 1]

in Chemical Formula 1,
R, a substituent positioned at the 6-position or 7-position of a coumarin ring of Chemical Formula 1, includes a $C_{8-50}$ aryl group.

2. The coumarin-based derivative compound of claim 1, wherein: the aryl group includes at least one of selected from the group consisting of a, an anthryl group, a naphthyl group, a phenanthryl group, an indene group, an azulene group, a fluorenyl group, a tetracene group, a triphenylene group, a pyrene group, a chrysene group, a pentacene group, a tetraphenylene group, a hexaphene group, a rubicene group, a coronene group, a trinaphthylene group, a pyranthrene group, a fluoranthene group, a benzofluoranthene group, a naphthacene group, and a coronyl group.

3. A fluorescent composition comprising the coumarin-based compound of claim 2.

4. The coumarin-based compound of claim 1, wherein: the coumarin-based derivative compound, includes at least one of selected from the group consisting of

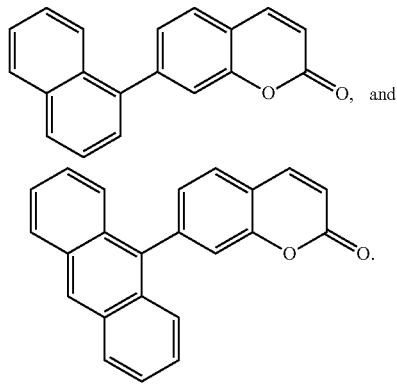

5. A fluorescent composition comprising the coumarin-based compound of claim 4.

6. A preparation method of the coumarin-based derivative compound of claim 1, the preparation method comprising:
reacting a coumarin-based compound represented by Chemical Formula 2 with $C_{8-50}$ aryl boronic acid in the presence of a palladium catalyst:

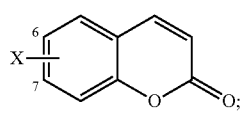

[Chemical Formula 2]

in Chemical Formula 2,
X is halogen positioned at the 6-position or 7-position of a coumarin ring of Chemical Formula 2.

7. The preparation method of claim 6, wherein: the aryl group includes at least one of selected from the group consisting of an anthryl group, a naphthyl group, a phenanthryl group, an indene group, an azulene group, a fluorenyl group, a tetracene group, a triphenylene group, a pyrene group, a chrycene group, a pentacene group, a tetraphenylene group, a hexaphene group, a rubicene group, a coronene group, a trinaphthylene group, a pyranthrene group, a fluoranthene group, a benzofluoranthene group, a naphthacene group, and a coronyl group.

8. A fluorescent composition comprising the coumarin-based compound of claim 1.

9. The fluorescent composition of claim 8, further comprising a semiconducting polymer.

10. The fluorescent composition of claim 9, further comprising an electron donor dopant.

11. The fluorescent composition of claim 9, wherein: the semiconducting polymer includes at least one of selected from the group consisting of a poly(N-vinylcarbozole)-based polymer, a poly(aniline)-based polymer, a poly(pyrrole)-based polymer, and a poly(thiophene)-based polymer.

12. The fluorescent composition of claim 9, wherein: fluorescence is emitted by transition from an n-π* singlet state to an exciplex state.

13. The fluorescent composition of claim 12, wherein: emitted fluorescent peak energy is proportional to a difference between an oxidation potential (Eox) value of the semiconducting polymer and an excited-state reduction potential (E*red) value of the coumarin-based compound.

14. The fluorescent composition of claim 12, wherein: an oxidation potential of the semiconducting polymer is smaller than an oxidation potential of the coumarin-based compound.

15. The fluorescent composition of claim 8, wherein: as the number of carbon atoms in the aryl group included in the coumarin-based compound is increased, a π conjugation length is increased, and an energy level of an n-π* singlet state is increased.

16. The fluorescent composition of claim 8, wherein: a level of an n-π* singlet state of the coumarin-based compound is higher than that of at least one of an ICT singlet state and an exciplex singlet state.

17. The fluorescent composition of claim 16, wherein: fluorescence is emitted by transition from the n-π* singlet state to the ICT singlet state.

18. The fluorescent composition of claim 17, wherein: a difference between an oxidation potential value and a reduction potential value of the coumarin-based compound is larger than emitted fluorescence energy.

19. The fluorescent composition of claim 16, wherein: in the n-π* singlet state, fluorescence weaker than fluorescence emitted in the ICT singlet state and the exciplex singlet state is emitted.

* * * * *